US012716895B2

(12) United States Patent
Hasan et al.

(10) Patent No.: US 12,716,895 B2
(45) Date of Patent: Aug. 25, 2026

(54) LOW VOLTAGE REDUCED GRAPHENE OXIDE (RGO)-BASED BIOSENSOR

(71) Applicant: Khalifa University of Science and Technology, Abu Dhabi (AE)

(72) Inventors: Shadi Wajih Hasan, Abu Dhabi (AE); Habiba Alsafar, Abu Dhabi (AE); Ahmed Fayez Yousef, Abu Dhabi (AE); Vijay Kumar Shankarayya Wadi, Abu Dhabi (AE); Lina Tizani, Abu Dhabi (AE); Dana Kadadou, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 925 days.

(21) Appl. No.: 17/966,051

(22) Filed: Oct. 14, 2022

(65) Prior Publication Data

US 2024/0125781 A1 Apr. 18, 2024

(51) Int. Cl.

| | |
|---|---|
| ***G01N 33/569*** | (2006.01) |
| ***B05D 7/00*** | (2006.01) |
| ***G01N 27/12*** | (2006.01) |
| ***G01N 33/543*** | (2006.01) |

(52) U.S. Cl.

CPC ....... *G01N 33/56983* (2013.01); *B05D 7/586* (2013.01); *G01N 27/125* (2013.01); *G01N 33/5438* (2013.01)

(58) Field of Classification Search

CPC ......... G01N 33/5438; G01N 33/56983; G01N 27/125

See application file for complete search history.

(56) References Cited

U.S. PATENT DOCUMENTS 4,839,017 A * 6/1989 Taniguchi .............. C08G 65/44 435/817

FOREIGN PATENT DOCUMENTS

WO WO-2022015814 A1 * 1/2022 ........... G01N 27/447

OTHER PUBLICATIONS

G. Seo, Rapid Detection of COVID-19 Causative Virus (SARS-CoV-2) in Human Nasopharyngeal Swab Specimens Using Field-Effect Transistor-Based Biosensor, AVS Nano 2020(14), pp. 5135-5142 (Year: 2020).*

L. Zhang, Recent Advances in Emerging 2D Material-Based Gas Sensors: Potential in Disease Diagnosis, Advanced Materials Interfaces, 2019(6), 1901329, pp. 1-27 (Year: 2019).*

M. Cotten, Evolution of increased positive charge on the SARS-CoV-2 spike protein may be adaptation to human transmission, iSicence, 2023(26), 106230, pp. 1-14 (Year: 2023).*

R. Singh, Label-free Detection of Influenza Viruses using a Reduced Graphene Oxide-based Electrochemical Immunosensor Integrated with a Microfluidic Platform., Scientific Reports, 2017(7), 42771, pp. 1-11 (Year: 2017).*

(Continued)

*Primary Examiner* — C. Sun

(74) *Attorney, Agent, or Firm* — Billion & Armitage

(57) ABSTRACT

In some embodiments, a method includes applying an analyte to a rGO biosensor configured to bind to the analyte; applying a DC voltage to the rGO biosensor, wherein the DC voltage is +0.0008 V to +0.005 V for a negatively charged analyte; or −0.005 V to −0.0008 for a positively charged analyte; and monitoring an electrical signal from the rGO biosensor for a response to the analyte.

18 Claims, 28 Drawing Sheets

(56) References Cited

OTHER PUBLICATIONS

Aguannoa, Ryan , et al., "MERS: Progress on the global response, remaining challenges and the way forward", Antiviral Research 159 (2018) 35-44.
Antipchik, Mariia , et al., "An electrochemical biosensor for direct detection of hepatitis C virus", Analytical Biochemistry 624 (2021) 114196.
Baker, Rachel E., "Infectious disease in an era of global change", Nature Reviews | Microbiology, Oct. 13, 2021, 13 pages.
Becerril, Héctor A., et al., "Evaluation of Solution-Processed Reduced Graphene Oxide Films as Transparent Conductors", ACS Nano, vol. 2, No. 3, 2008, 463-470.
Broughton, James P., et al., "CRISPR-Cas12-based detection of SARS-CoV-2", Nature Biotechnology | vol. 38 | July 872 2020 | 870-874 | www.nature.com/naturebiotechnology.
Faridi, Uzma , "Middle East respiratory syndrome coronavirus (MERS-CoV): Impact on Saudi Arabia, 2015", Saudi Journal of Biological Sciences (2018) 25, 1402-1405.
Gao, Yakun , et al., "Rapid and sensitive triple-mode detection of causative SARS-CoV-2 virus specific genes through interaction between genes and nanoparticles", Analytica Chimica Acta 1154 (2021) 338330.
Hasan, Shadi W., et al., "Detection and quantification of SARS-CoV-2 RNA in wastewater and treated effluents: Surveillance of COVID-19 epidemic in the United Arab Emirates", Science of the Total Environment 764 (2021) 142929.
Hata, Akihiko , et al., "Detection of SARS-CoV-2 in wastewater in Japan during a COVID-19 outbreak", Science of the Total Environment 758 (2021) 143578.
Hidayah, N. M. S. , et al., "Comparison on graphite, graphene oxide and reduced graphene oxide: Synthesis and characterization", AIP Conference Proceedings 1892, 150002 (2017); doi: 10.1063/1.5005764.
Hilgenfeld, Rolf , et al., "From SARS to MERS: 10 years of research on highly pathogenic human coronaviruses", Antiviral Research 100 (2013) 286-295.
Kadadou, Dana , et al., "Detection of SARS-CoV-2 in clinical and environmental samples using highly sensitive reduced graphene oxide (rGO)-based biosensor", Chemical Engineering Journal (2022), doi: https://doi.org/10.1016/j.cej.2022.139750.
Kadadou, Dana , et al., "Optimization of an rGO-based biosensor for the sensitive detection of bovine serum albumin: Effect of electric field on detection capability", Chemosphere 301 (2022) 134700.
Kadadou, Dana , et al., "Recent advances in the biosensors application for the detection of bacteria and viruses in wastewater", Journal of Environmental Chemical Engineering 10 (2022) 107070.
Karakus, Erman , et al., "Colorimetric and electrochemical detection of SARS-CoV-2 spike antigen with a gold hanoparticle-based biosensor", Analytica Chimica Acta 1182 (2021) 338939.
Kumar, M.S. , et al., "Electrochemical sensing of SARS-CoV-2 amplicons with PCB electrodes", Sensors & Actuators! B. Chemical 343 (2021) 130169.
Langone, M. , et al., "SARS-CoV-2 in water services: Presence and impacts", Environmental Pollution 268 (2021) 115806.
Ni, Jingbo , et al., "Facile construction of poly(styrene-acrolein)/reduced graphene oxide nanocomposites via in-situ reduction and its corrosion resistance properties in waterborne acrylic resin coating", Chemical Physics Letters 772 (2021) 138570.
Ramírez-Chavarría, Roberto G., et al., "Loop-mediated isothermal amplification-based electrochemical sensor for detecting SARS-CoV-2 in wastewater samples", Journal of Environmental Chemical Engineering 10 (2022) 107488.
Rimoldi, Sara Giordana, et al., "Presence and infectivity of SARS-CoV-2 virus in wastewaters and rivers", Science of the Total Environment 744 (2020) 140911.
Seo, Giwan , et al., "Rapid Detection of COVID-19 Causative Virus (SARS-CoV-2) in Human Nasopharyngeal Swab Specimens Using Field-Effect Transistor-Based Biosensor", ACS Nano 2020, 14, 5135-5142.
Sharma, Sanjeev , et al., "2D photonic crystal based biosensor for the detection of chikungunya virus", Optik—International Journal for Light and Electron Optics 237 (2021) 166575.
Tene, Talia , et al., "Toward Large-Scale Production of Oxidized Graphene", Nanomaterials 2020, 10, 279; doi:10.3390/nano10020279.
Thanihaichelvan, M. , et al., "Selective and electronic detection of COVID-19 (Coronavirus) using carbon hanotube field effect transistor-based biosensor: A proof-of-concept study", Materials Today: Proceedings, https://doi.org/10.1016/j.matpr.2021.05.011.
Torres, Marcelo D. T., et al., "Low-cost Biosensor for Rapid Detection of SARS-CoV-2 at the Point-of-Care", Matter (2021), doi: https://doi.org/10.1016/j.matt.2021.05.003.
Ueno, Keiji , et al., "Solution Processed Graphene Transparent Conductive Film", 49-52.
Wang, Shiyu , et al., "Graphene field-effect transistor biosensor for detection of biotin with ultrahigh sensitivity and specificity", Biosensors and Bioelectronics 165 (2020) 112363.
Wu, Guangfu , et al., "Doping Effects of Surface Functionalization on Graphene with Aromatic Molecule and Organic Solvents", Applied Surface Sciencehttp://dx.doi.org/10.1016/j.apsusc.2017.07.048.
Yin, Kun , et al., "Multiplexed colorimetric detection of SARS-COV-2 and other pathogens in wastewater on a 3D printed integrated microfluidic chip", Sensors & Actuators: B. Chemical 344 (2021) 130242.
Zhang, Meiling , et al., "Ultrasensitive detection of SARS-CoV-2 spike protein in untreated saliva using SERS-based biosensor", Biosensors and Bioelectronics 190 (2021) 113421.
Zhao, Hui , et al., "Ultrasensitive supersandwich-type electrochemical sensor for SARS-CoV-2 from the infected COVID-19 patients using a smartphone", Sensors & Actuators: B. Chemical 327 (2021) 128899.
Zhu, Qian , et al., "A colorimetric sandwich-type bioassay for SARS-CoV-2 using a hACE2-based affinity peptide pair", Journal of Hazardous Materials 425 (2022) 127923.

* cited by examiner

Synthetic S1 Protein
2702
2700
100

2715
2710
2711
0.5 fg/mL
2712
1 fg/mL
2713
$10^3$ fg/mL
2714
$10^4$ fg/mL
$10^5$ fg/mL
Normalized Current
-0.2 0.0 0.2 0.4 0.6 0.8 1.0 1.2 1.4 1.6 1.8
0 50 100 150 200 250
Time (s)

2720
2722
Normalized Current
0.0 0.2 0.4 0.6 0.8 1.0 1.2 1.4
0.1 1 10 100 1000 10000 100000 1000000
Concentration (fg/mL)

2730
2731
BSA
2732
Vegan Protein
2733
SARS-CoV-2 S1 Protein
2734
Glucosidase
2735
SARS-CoV-2 N Protein
Normalized Current
0.00 0.02 0.04 0.06 0.08 0.10 0.12 0.14 0.16 0.18 0.20
0 50 100 150 200 250
Time (s)

LOW VOLTAGE REDUCED GRAPHENE OXIDE (RGO)-BASED BIOSENSOR

BACKGROUND

Techniques that may be utilized for pathogenic testing/identification includes quantitative RT-PCR (qRT-PCR), enzyme-linked immunosorbent assay (ELISA), and lateral flow immunoassay tests. qRT-PCR is often used and remains the gold standard for the diagnosis of SARS-CoV-2 infection, due to its high accuracy and sensitivity. However, certain limitations drive the need for the development of new and alternative diagnostic methods. For example, qRT-PCR requires well-equipped laboratories and highly trained personnel, and a turnaround time of 4-6 hours.

Testing for pathogens in wastewater is complex because municipal wastewater includes solutes and suspended solids that can interfere with testing. As such, novel diagnostic methods and devices that are fast, accurate, sensitive, do not require capital expenditures and highly trained personnel, and which may be used to test wastewater are desirable.

SUMMARY

In some embodiments, a method includes applying an analyte to a rGO biosensor configured to bind to the analyte; applying a DC voltage to the rGO biosensor, wherein the DC voltage is +0008V to +0.005V for a negatively charged analyte; or −0.005V to −0.0008 for a positively charged analyte; and monitoring an electrical signal from the rGO biosensor for a response to the analyte.

Embodiments further include a graphene oxide substrate for fabricating a rGO biosensor. The graphene oxide substrate includes a base and five or more layers of graphene oxide on the base. The five or more layers may be formed by a graphene oxide solution with a concentration of 2 mg/mL.

Embodiments include a method that includes depositing five or more layers of graphene oxide (GO) onto a base; reducing the GO to reduced graphene oxide (rGO) to form a rGO substrate; and immobilizing bioreceptors to form a rGO biosensor. Embodiments further include a rGO biosensor manufactured by the method.

BRIEF DESCRIPTION OF DRAWINGS

This written disclosure describes illustrative embodiments that are non-limiting and non-exhaustive. Reference is made to illustrative embodiments that are depicted in the figures, in which:

FIG. 15A is an SEM micrograph of rGO surface. FIG. 15B is a SEM micrograph of PBASE functionalized surface. FIG. 15C is an SEM micrograph of an antibody immobilized surface.

FIG. 26A is graph comparing the X-Ray diffraction of GO and rGO. FIG. 26B is a graph of a Raman spectra of GO, rGO, and rGO/PBASE. FIG. 26C is a graph of the current-voltage characteristics of the rGO biosensor throughout functionalization. FIG. 26D illustrates Atomic Force Microscopy images and surface roughness profiles of rGO and rGO/PBASE over a 2 μm line scan.

FIG. 27A illustrates a detection scheme of rGO biosensor towards SARS-CoV-2 S1 protein, according to some embodiments. FIG. 27B illustrates a graph of the real-time response of the rGO biosensor to different concentrations of SARS-CoV-2 S1 protein in phosphate buffered saline (PBS). FIG. 27C illustrates the concentration-dependent response curve for the rGO biosensor. FIG. 27D illustrates the response of the rGO biosensor to BSA, vegan, glucosidase, and SARS-CoV-2 N protein.

FIG. 28A illustrates a schematic diagram of municipal wastewater sample analysis using qRT-PCR, rapid antigen tests, or the rGO biosensor. FIG. 28B illustrates a bar graph of the SARS-CoV-2 concentrations in wastewater samples as determined by qRT-PCR. FIG. 28C illustrates a graph of a real-time response of the rGO biosensor to wastewater sample. FIG. 28D illustrates a real-time response of the rGO biosensor and rapid antigen tests to wastewater samples.

DETAILED DESCRIPTION

Embodiments of the present disclosure describe a reduced graphene oxide (rGO) biosensor that can detect protein analytes present at very low concentrations in an aqueous solution. An electrochemical reaction occurs in the presence of the target protein/analyte is converted into a detectable electrical signal. The rGO biosensor may be used for many applications and instead of diagnostic devices that are slow, require capital expenditures, and highly trained personnel. For example, the rGO biosensor may be used at a medical or screening facility point-of-care or in the field. The rGO biosensor may also be utilized to provide real-time data that may be analyzed. The rGO biosensor is cost-effective and can be used at room temperature, with minimal equipment and consumable requirements, which contributes to its ease of use. Additionally, the rGO biosensor is highly scalable and its fabrication may be automated for mass production. Finally, the fabrication procedure described is highly modular, and the device can be quickly modified and tested to rapidly detect future pandemic outbreaks or other analytes of interest.

The rGO biosensor may also be used to detect protein analytes in more complex situations, such as raw municipal wastewater samples. Detection of protein analytes in wastewater may be conducted without the need for another sample pre-filtration or processing steps. Furthermore, the rGO biosensor may be integrated into wastewater pipelines as an early warning system and allow appropriate control strategies to be taken in time to prevent an outbreak of disease.

A rGO biosensor as described herein is rapid, sensitive and utilize a low applied voltage. For example, a rGO biosensor configured to detect BSA protein, was observed to have a limit of detection (LOD) of 1 fg/mL at an applied voltage of 0.0008 V and a saturation limit of 1 mg/mL. As another non-limiting example, a rGO biosensor configured to detect SARS-CoV-2 was observed to have a LOD of 0.5 fg/mL in SARS-CoV-2 S1 protein in PBS, 2.91 genome copies/mL in municipal wastewater samples, and an average response time of 240 ms.

Figure 1:
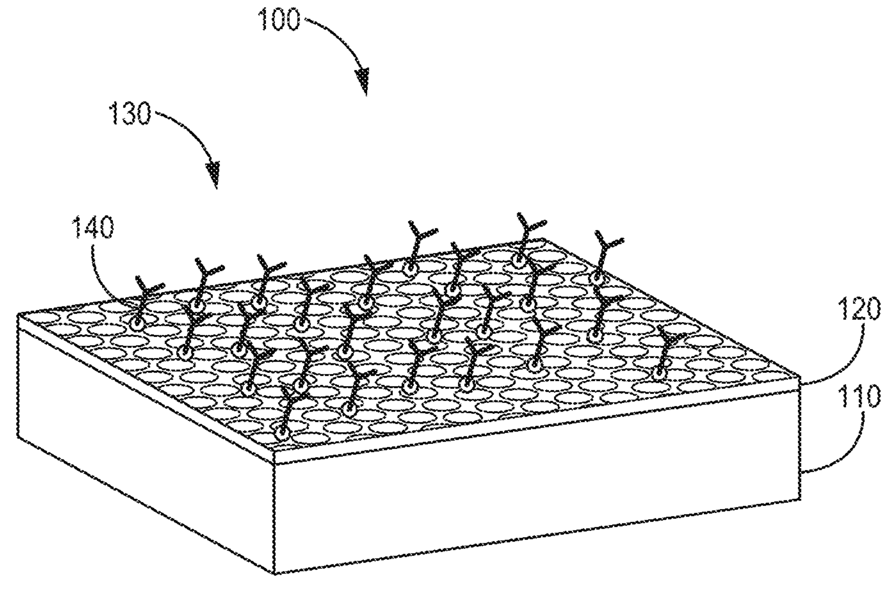
FIG. 1 illustrates a perspective view of a reduced graphene oxide (rGO) biosensor, according to some embodiments.

FIG. 1 illustrates a perspective view of a rGO biosensor 100, according to some embodiments of this disclosure. The biosensor 100 includes a substrate 110, an rGO layer/surface 120 adjacent to the substrate/base 110, and bioreceptors 130 immobilized on the rGO layer 120 via a linker molecule 140.

Figure 2:
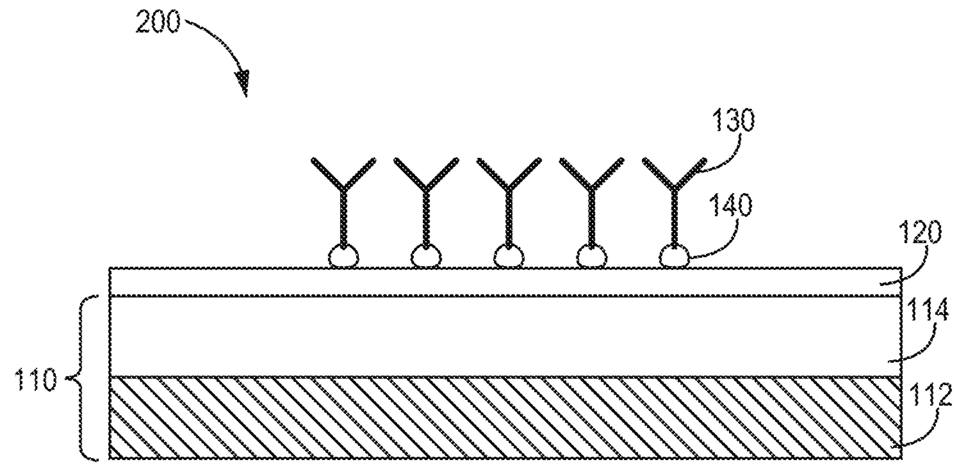
FIG. 2 illustrates a cross-sectional view of a reduced graphene oxide (rGO) biosensor, according to some embodiments.

As illustrated in FIG. 2, the substrate 110 may include a base layer 112 and a top layer 114.

In some embodiments, the rGO biosensor 100 may be stored at 5-20° C. In one non-limiting example, the rGO biosensor 100 is stored at 5° C. The rGO biosensor 100 may have any suitable shape and/or size. For example, the biosensor 100 may be circular, square, or rectangular. The rGO biosensor 100 may have a length of 10-30 mm, a width of 10-30 mm, and a height of 1-2 mm. In some embodiments, the rGO biosensor 100 may include an encapsulation layer (not illustrated). Embodiments of a rGO biosensor 100 with an encapsulation layer may have a height of 1-3 cm. In one non-limiting example, the size of the rGO biosensor 100 is 20×20 $mm^2$. As another example, the size of a rGO biosensor 100 configured for use in a wastewater pipeline may be 100 $mm^2$ to 900 $mm^2$.

The substrate 110 may have a thickness of 0.5-1.5 mm. In some implementations, the substrate 110 includes silicon (Si) with silicon dioxide ($SiO_2$), or glass. The base layer 112 may have a thickness of 500-600 μm and the top layer 114 may have a thickness of 100-300 mm. In a non-limiting example, the top layer 114 is 300 nm thick. The base layer 112 may be a layer of Si and the top layer 114 may be a layer of $SiO_2$. In some implementations, a Si wafer may be utilized for the Si base layer 112. In one implementation, the $SiO_2$ layer 114 is positioned between the Si base layer 112 and the rGO layer 120. The rGO layer 120 may have a thickness of 20-60 nm.

The rGO layer 120 may have a thickness of 20-60 nm. The thickness of rGO film may be measured using atomic force microscopy tool. The rGO layer 120 may be formed from one or more layers of GO. In some embodiments, the rGO layer 120 was formed from seven layers of GO. In further embodiments, the solution of GO forming the one or more layers of GO has a concentration of 2 mg/mL. An exemplary method to produce the GO solution is discussed below in greater detail. In one example, the rGO layer 120 was formed by depositing seven layers of a GO solution with a concentration of 2 mg/mL.

The bioreceptors 130 are configured to bind a desired target/analyte. Bioreceptors 130 include antibodies, proteins, enzymes, affinity binding receptors, nucleic acids. The present discussion will focus on utilizing antibodies for the bioreceptors 130. Any suitable antibody 130 may be utilized. For example, antibodies utilized for ELISA may be utilized for antibodies 130. In some implementations, the antibodies 130 have binding affinity to SARS-CoV-2. For example, the antibodies 130 may have a binding affinity to the S1 protein of SARS-CoV-2.

Fabricating a rGO Biosensor

Figure 3:
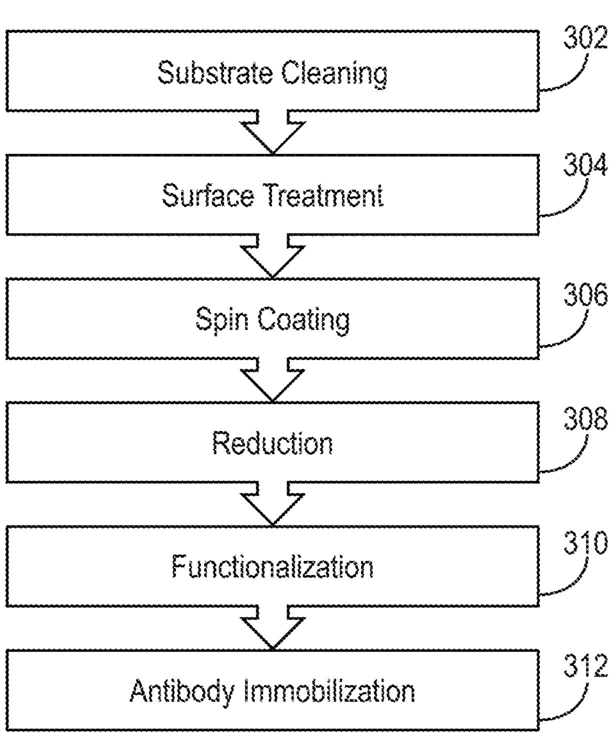
FIG. 3 illustrates a flow chart of a method 200 of forming a rGO biosensor, according to some embodiments.
Figure 4:
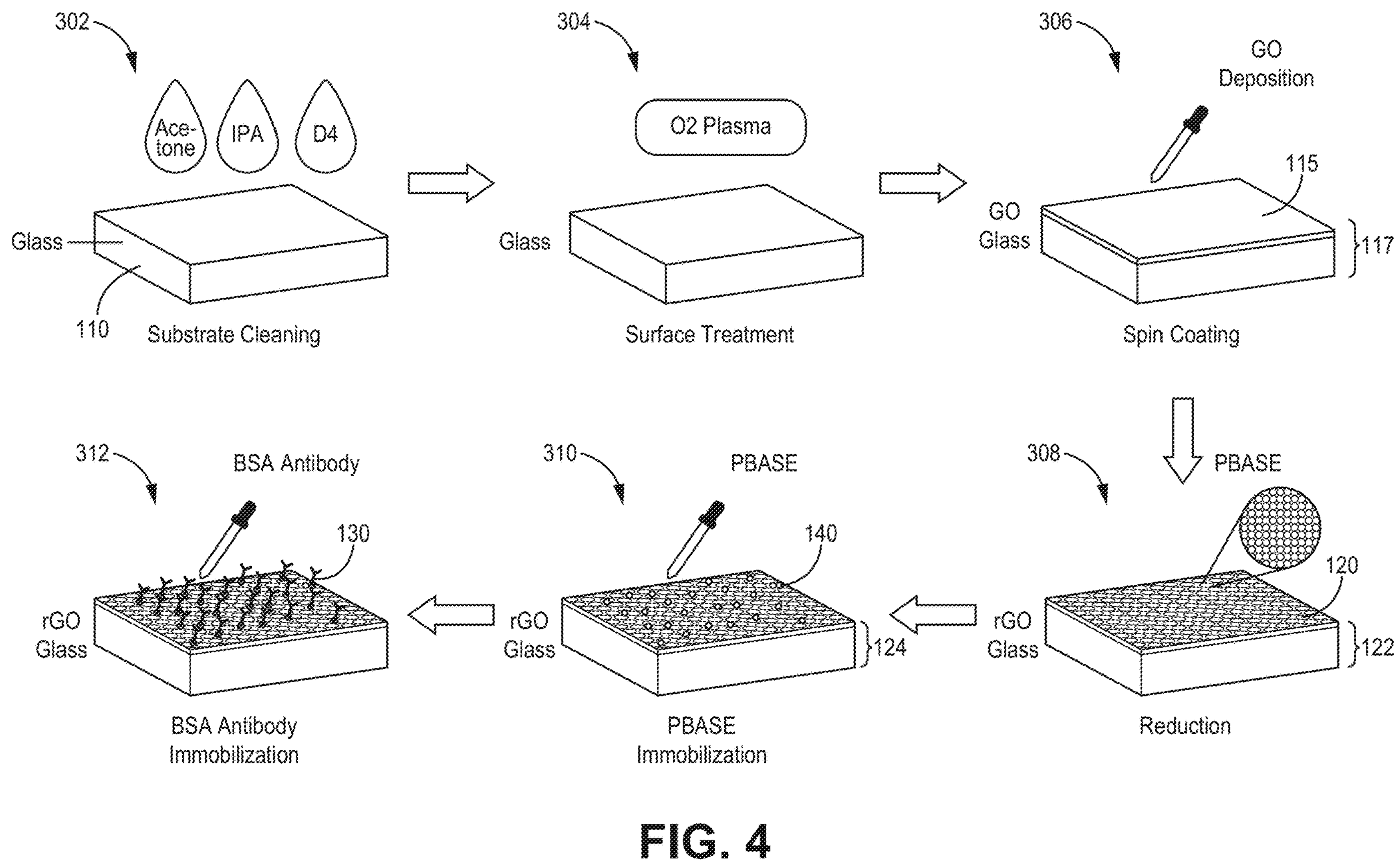
FIG. 4 illustrates a schematic of a rGO biosensor fabrication process, according to some embodiments.

FIG. 3 illustrates a flow chart of a fabrication method 300 of fabricating the rGO biosensor 100, according to some embodiments, and FIG. 4 is a schematic of a rGO biosensor fabrication process utilizing method 300, according to some embodiments. In some implementations of method 300, 2×2 $cm^2$ substrates 110 are utilized.

During Step 302, the substrate 110 is cleaned. Step 302 may include applying one or more cleaning solutions to the substrate 110. Step 302 may further include sonicating the substrate 110. In one aspect, Step 302 suppresses surface contaminants. In one example, the substrate 110 is cleaned consecutively with acetone, isopropyl alcohol (IPA), and DI water for 2 minutes each, using a bath sonicator.

During Step 304, the surface of the cleaned substrate 110 undergoes a treatment to modify the surface properties of the substrate 110. In one aspect, Step 304 suppresses surface contamination, improves wettability/hydrophilicity, and/or may avoid aggregation of a GO solution applied to the substrate 110. In some implementations, a physical treatment is utilized to modify the surface properties of the substrate. In one aspect, plasma treatment aids in the formation of uniform GO films on the substrate 110. In another aspect, the physical treatment does not utilize chemicals that may be corrosive. In one example, the physical treatment includes using plasma treatment (PT) for 2 minutes. In other implementations, a chemical treatment is utilized to modify the surface properties of the substrate. In one example, the chemical treatment includes cleaning the surface with a piranha solution—a mixture of sulfuric acid ($H_2SO_4$) and hydrogen peroxide ($H_2O_2$).

During Step 306, a coated substrate 117 is formed (see FIG. 4). The coated substrate 117 may be formed by depositing one or more layers of GO 119 onto the cleaned, treated, substrate 110. In at least one embodiment, at least seven GO layers 119 is deposited. An exemplary method of GO synthesis is discussed below in greater detail. In some embodiments, an aqueous GO solution is spin-coated onto the substrate 110 in consecutive layers 119. In at least one embodiment, the GO solution has a concentration of 2 mg/mL. In one non-limiting example, seven layers of a 2 mg/mL solution of GO is spin-coated onto the substrate 110. In one aspect, spin-coating GO produces a uniform and highly oriented graphene thin film 119. Another aspect of utilizing spin-coating to deposit the one or more GO layers 119 is the resistance values of the biosensor 100 are stable. This is in contrast to a biosensor fabricated by drop-casting the one or more GO layers onto the substrate 110. One non-limiting example of a spin coating method that may be utilized to deposit the GO solution includes three runs at 500, 800, and 1600 rpm for 40, 30, and 30 seconds. A benefit of this spin-coating method is that it produces a continuous and uniform GO layer 119. In one aspect, a GO layer 119 formed via this spin coating method does not include relatively rough surfaces due to the overlapping of GO layers.

In at least one embodiment, after a GO layer 115 is deposited, the surface is dried, for example by heating. For example, after a GO layer 115 is deposited, the coated substrate is placed on a hot plate at 100° C. for 30 seconds and after the final GO layer 115 is deposited the coated substrate is placed on a hot plate at 100° C. for 1 hour. In one aspect, drying the surface enhances the adhesion of the GO layer 115 to the substrate 110. In another aspect, drying avoids losses in the one or more layers of deposited GO 119.

During Step 308, the one or more layers of GO 115 are reduced to rGO 120 to form a substrate 122 with a rGO layer (hereinafter a rGO substrate). In one implementation, thermal reduction is utilized to reduce the one or more layers of GO 115 to rGO 120. For example, the one or more layers of GO 115 are reduced to rGO 120 by placing the coated substrate 117 in a horizontal tube furnace under an $N_2$ atmosphere. One exemplary program for the horizontal tube furnace to reduce the GO includes heating the coated substrate 117 from room temperature to 450° C. at a rate of 7° C./minute and then remain at 450° C. for 1.5 hours. In one aspect, slow heating to 450° C. reduces the GO to rGO whereas heating to a temperature above 550° C. may decompose the GO completely. [In some embodiments, Step 308 results in a 35-50% weight loss for the GO layer 115. In another aspect, thermal reduction is environmentally friendly, there is no risk of surface contamination, and due to the slow heating process the GO sheets stay intact on the substrate surface. In contrast, chemical reduction involves utilizing liquid reducing agents under heating and steering and, the process peels off the GO from the substrate surface. Additionally, cleaning of the reducing agents is required after chemical reduction which further damages the rGO surface. In some implementations, the rGO substrate 122 is stored before proceeding to Step 310. The rGO substrate 122 may be stored at room temperature.

During Step 310, the surface of the rGO layer of the rGO substrate 122 is functionalized with a linker molecule 140 to form a functionalized substrate 124. An example of a suitable linker molecule 140 is 1-pyrenebutyric acid N-hydroxysuccinimide ester (PBASE, $C_{24}H_{19}NO_4$; $M_w$:385.41 g/mol). PBASE is a non-covalent linker and exhibits dual functionality with pyrene and succinimidyl ester groups. The N-hydroxysuccinimide ester of PBASE may react with amino groups of protein molecules. When the rGO surface 120 is exposed to PBASE, strong binding to the rGO surface 120 may occur due to R-stacking and van der Waals forces. A 2 mM PBASE solution in methanol may be prepared using a bath sonicator for 5 minutes. To functionalize the rGO substrate 122 with a PBASE linker 140, the rGO substrate 122 is dipped in PBASE for 1 hour at room temperature, rinsed in methanol, rinsed with DI water, and dried at 50° C. on a hot plate for 2 minutes. In one example, the rGO substrate 122 is rinsed three times in methanol.

During Step 312, antibodies 130 are immobilized onto the surface of the functionalized substrate 124 to form the rGO biosensor 100. For example, the surface of the functionalized substrate 124 may be chemically modified with antibodies. The functionalized substrate 124 may be soaked in a solution/bath of antibodies 130. The antibody solution may include PBS or methanol. The functionalized substrate 124 may be soaked for 1 to 12 hours. For maximum immobilization, the device may be soaked in the solution of antibodies for at least eight (8) hours. As one example, the functionalized substrate 124 is exposed to a 150 μg/mL of BSA antibodies for 3.5 hours at room temperature. As another example, the functionalize substrate 124 is exposed to 250 μg/mL of S1 antibodies in PBS and left overnight. After exposing the functionalized substrate 124 to the antibody solution, any non-reacted antibody may be removed by rinsing with PBS and/or DI water.

Optionally, after Step 312, the rGO biosensor 100 may be capped. Capping the device may prevent possible nonspecific binding of the protein/analyte to unreacted linker molecules. For example, PBASE molecules have a N-hydroxysuccinimide group that can react with amino groups in protein molecules. In one aspect, utilizing a capping solution improves selectivity and specific binding by capping these sites. Examples of capping solutions include glycine solutions. The device may be soaked in a capping solution for 30-60 minutes. In one non-limiting example, capping a device utilizing PBASE linker molecules includes immersing/soaking the device in 20 mg/mL of glycine in DI water for 30 minutes and then rinsing with DI water.

Optionally, method 300 may include fabricating the substrate 110 before Step 302. In some implementations, fabricating the substrate 110 includes depositing a layer 114 of $SiO_2$ onto a Si base 112 to form the substrate 110. In some embodiments, the Si base 112 is a silicon wafer. The $SiO_2$ layer 114 may be thermally deposited onto the Si layer 112. Other techniques to deposit the $SiO_2$ layer 114 include plasma enhanced chemical vapor deposition. In a non-limiting example, the Si wafer 112 with a $SiO_2$ layer 114 may be cut into a plurality of substrates 110. For example, a Si wafer 112 with a diameter of 4 inches may be divided into 8 to 10 substrates 110. Techniques that may be utilized to cut the Si wafer 112 into a plurality of substrates 110 include cutting using a diamond pen or semiconductor wafer dicing. Utilizing a Si wafer 112 to fabricate the rGO biosensor 100 is one way the method to fabricate the rGO biosensor 100 may be scaled up and/or automated.

GO Synthesis Via the Simplified Hummer Method

An exemplary method of GO synthesis from graphitic flakes utilizes the simplified Hummer's method. Briefly, 3 g of graphitic flakes and 9 g of $KMnO_4$ were slowly added to a solution of $H_2SO_4$:$H_3PO_4$ (360:40 mL, 1:9 ratio) in an ice bath for 20-30 minutes. The reaction mixture was then stirred for 3 days at room temperature to ensure oxidation, which was indicated by a change in the color of the solution from dark purple-green to dark green. The reaction was stopped by the slow addition of 35% $H_2O_2$ until the color changed to bright yellow, indicating graphite oxidation. The solution was then washed several times with 1 M (HCl) followed by deionized (DI) water until pH 5-6. The final obtained thick dark brown GO solution was stored at room temperature. The GO concentration was calculated by measuring the dry mass from a known volume of the GO solution.

Detection System

Figure 5:
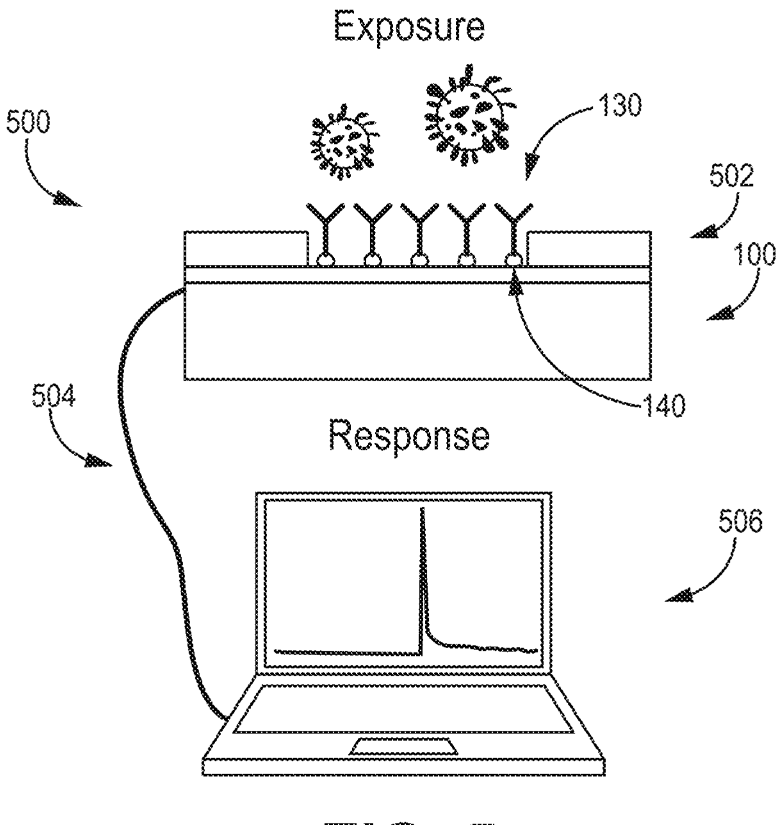
FIG. 5 illustrates a schematic detection system, according to some embodiments.

FIG. 5 illustrates a schematic of an embodiment of a detection system 500 utilizing a rGO biosensor 100. In some implementations, the detection system 500 is utilized to identify an outbreak or infection risk within a population.

The system 500 includes at least one rGO biosensor 100 and a computing platform 506. In some implementations, the rGO biosensor 100 further includes a probe 502. For example, the probe 502 may be coupled to the rGO layer 120 of the rGO biosensor 100. As illustrated in FIG. 5, the probe 502 is coupled to the upper surface of the rGO layer 120. The probe 502 is configured to apply a DC voltage to the biosensor 100 and/or to measure current. The probe 502 may be a four points probe—a four-terminal Kelvin sensor is one example (see e.g, source meter of FIG. 23). The probe 502 may be coupled to the rGO biosensor 100 by a conductive material. The conductive material may be silver, gold, or other conductive materials. In one example, the conductive material is a paste, e.g., a silver paste, or a coating deposited on the rGO biosensor 100.

The rGO biosensor 100 and the computing platform 506 are communicatively coupled to one another via a communication channel 504. Examples of computing platforms 606 include a tablet, a computer, and a smart phone. Data may be saved to memory and/or processed by the computing platform 506. For example, a present/real-time value for the current measured by the four-point probe 502 may be communicated to the computing platform 506. The computing platform 506 may include instructions stored in memory to calculate a normalized current value using the initial current value ($I_o$) and the real-time current (I) using Eq. (1):

$$\Delta I/I_o=(I-I_o)/I_o \quad (1)$$

In some implementations, at least one predetermined value for the normalized current is utilized to identify an outbreak or infection risk within a population.

Method of Utilizing a rGO Biosensor

Figure 6:
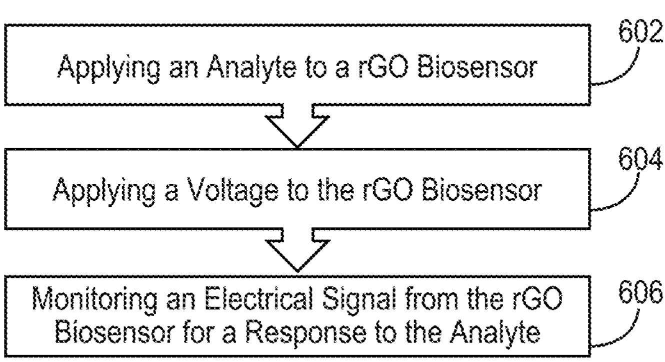
FIG. 6 illustrates a flow chart of a method 600 of utilizing a rGO biosensor, according to some embodiments.

FIG. 6 is a flowchart of a method 600 of utilizing a rGO biosensor 100 to detect a target analyte. In some implementations, the rGO biosensor 100 forms a part of a detection 500 as discussed above. At Step 602, an analyte is applied to the rGO biosensor 100. For example, the rGO biosensor 100 may be placed in a detection bath and a sample to be analyzed is applied to the detection bath. As another example, the rGO biosensor 100 may be placed in a wastewater pipe. As an additional example, a sample may be applied to the rGO biosensor 100.

At Step 604, a voltage is applied to the rGO biosensor 100. In some implementations, a probe 502 executes Step 604. In at least one embodiment, the applied voltage is a DC voltage. A negative applied DC voltage is utilized for a positively charged target analyte and a positive applied DC voltage is utilized for a negatively charged target analyte. The applied DC voltage may range from +0.0008 V to +0.005 V or −0.0005 to −0.0008.

At Step 606, an electrical signal from the rGO biosensor 100 is monitored for a response to the analyte. Monitoring for a response may include determining one or more normalized current values from one or more measured current values. In some implementations, a probe 502 executes Step 606. The normalized current value may be calculated using equation (1). In some implementations, a computing platform 506 executes Step 606. Monitoring for a response may include identifying a peak in the normalized current value, where the peak is an indication that the target analyte has been detected by the biosensor 100. Identifying a peak in the normalized current value may include graphing the normalized current value over time. In some implementations, the peak is identified when the normalized current values exceeds a predetermined value. In some implementations, a computing platform 506 executes Step 608.

Performance/Analysis of rGO Biosensor

Figure 7:
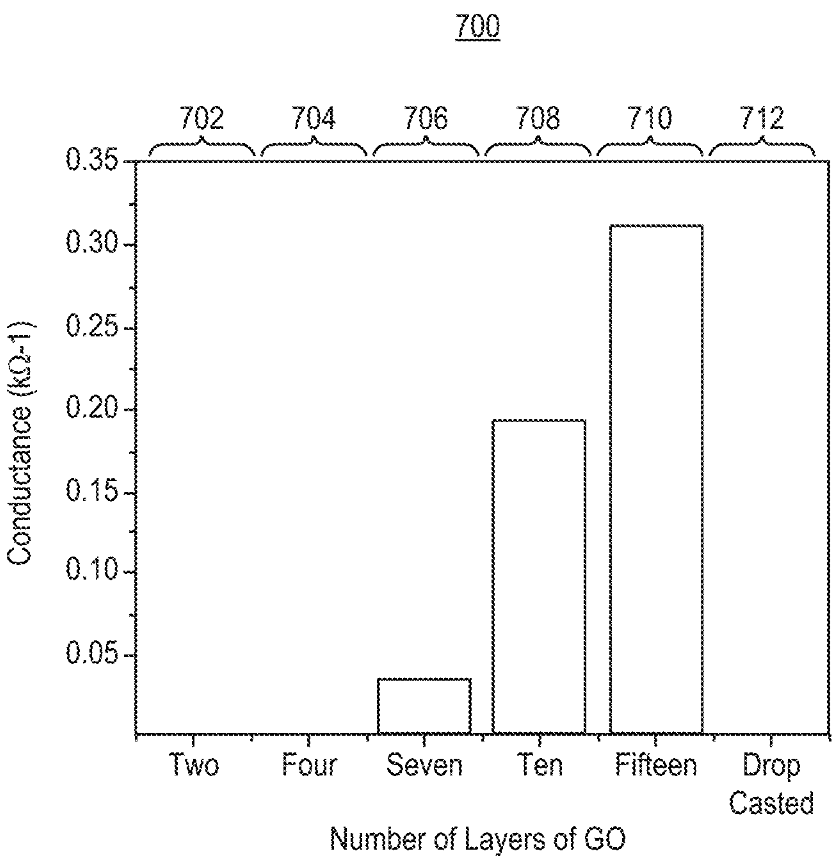
FIG. 7 illustrates a graph of conductance versus number of layers of GO, according to some embodiments.

FIG. 7 is a bar graph 700 of conductance ($k\Omega^{-1}$) after reduction versus the number of GO layers 120. The number of GO layers 120 investigated were two layers 702, four layers 704, seven layers 706, ten layers 708, and fifteen layers 701. The conductance of a GO layer 120 fabricated by drop coating 712 was also investigated. No conductance was observed for two rGO layers 702, four GO layers 704, or for GO deposited by drop casting 712. As illustrated in graph 700, the conductance increased with an increase in the number of GO layers with the observed conduction being the greatest for fifteen GO layers 710.

Figure 8:
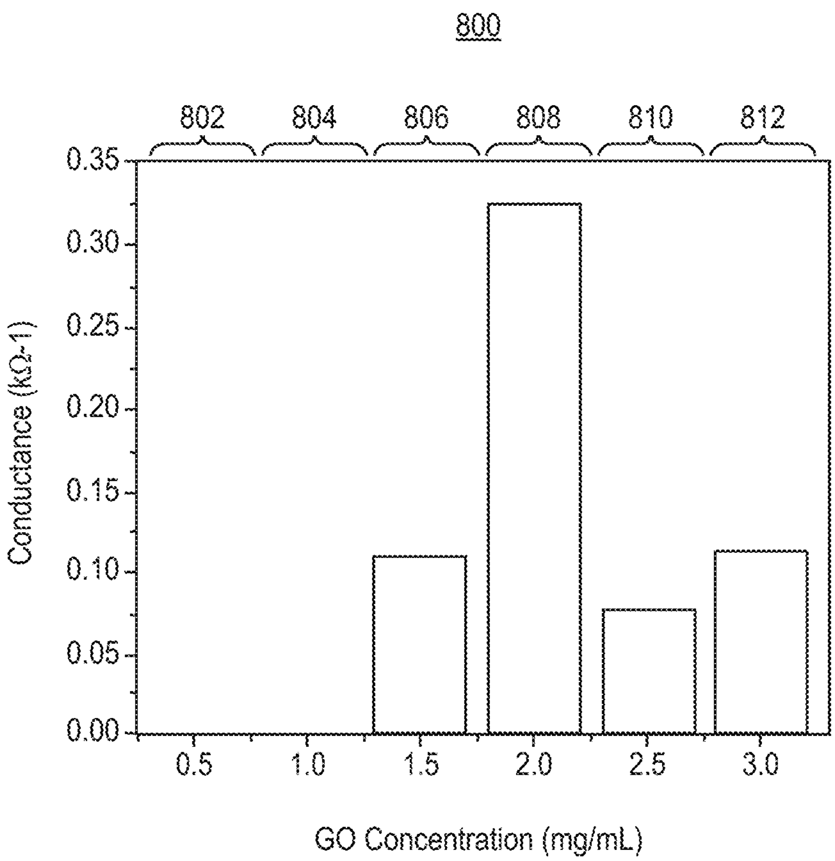
FIG. 8 illustrates a graph of conductance versus GO concentration, according to some embodiments.

FIG. 8 is a bar graph 800 of conductance ($k\Omega^{-1}$) after reduction versus GO concentration (mg/mL). The GO concentrations investigated were 0.5 mg/mL 802, 1.0 mg/mL 804, 1.5 mg/mL 806, 2.0 mg/mL 808, 2.5 mg/mL 810 and 3.0 mg/mL 812. Stable conductance values were not observed for 0.5 mg/mL 802 and 1.0 mg/mL 804. Stable conductance values were observed for 1.5 mg/ml 806, 2 mg/ml 808, 2.5 mg/ml 810, and 3 mg/mL 812, with a noticeably higher conductance in the sample prepared with 2 mg/mL. One aspect of graph 800 is that conductance is not a function of GO concentration.

Figure 9:
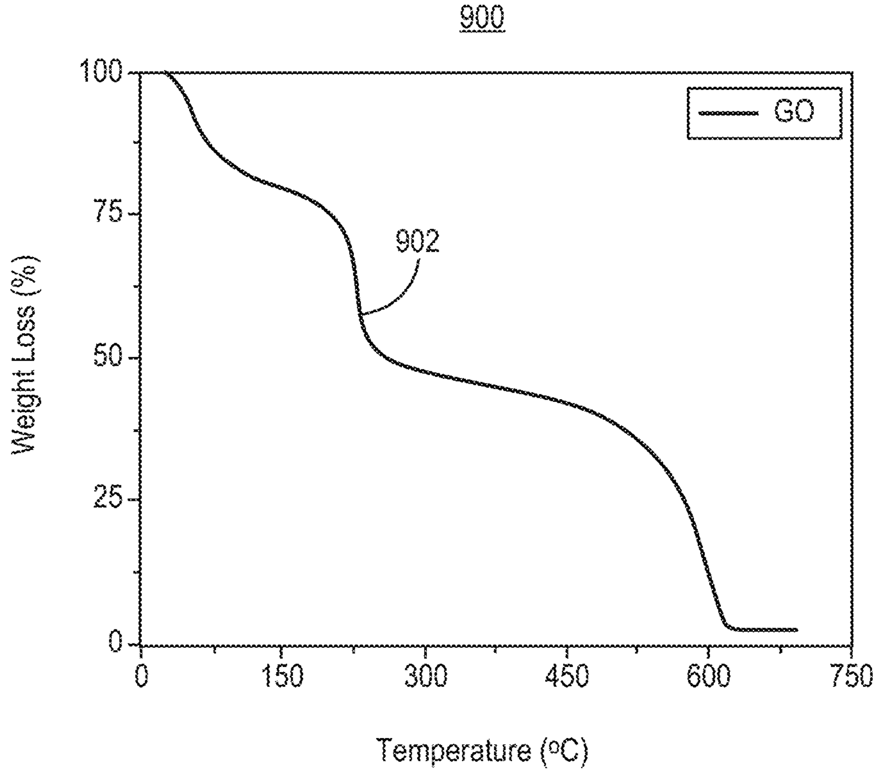
FIG. 9 illustrates a graph of the thermal reduction of deposited GO films, according to some embodiments.

FIG. 9 is a graph 900 illustrates experimental results from TGA analysis of the thermal reduction of deposited GO layers 119 at 450° C. under $N_2$ atmosphere. The sample was run from 25 to 700° C., during which loss in weight data was obtained. Heating was performed at a rate of 5° C./minute.

Figure 10:
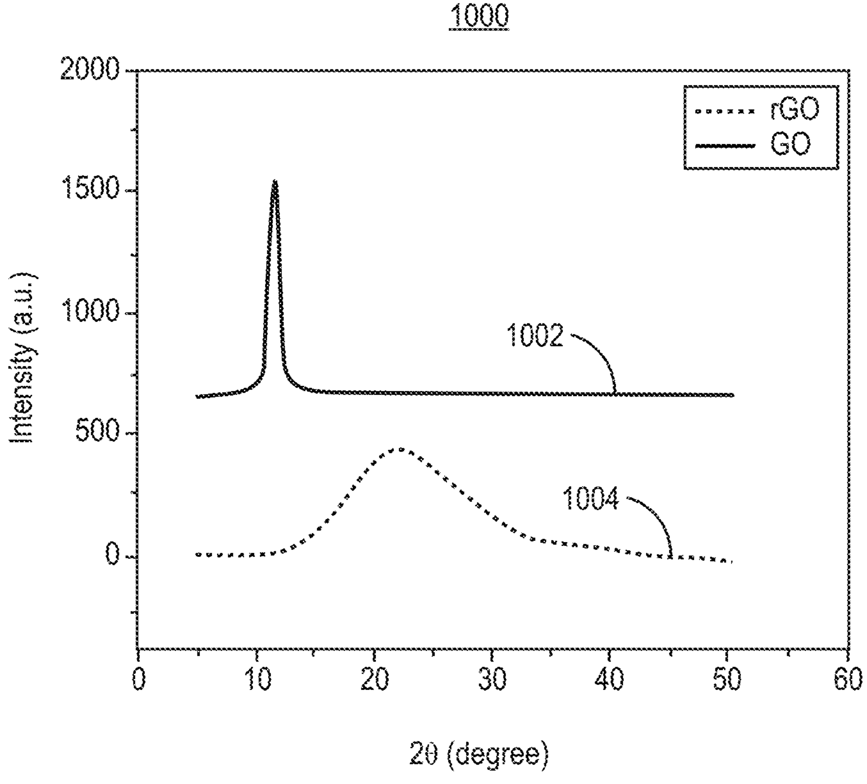
FIG. 10 illustrates a graph of X-ray diffraction (XRD) patterns of GO and rGO, according to some embodiments.

GO reduction was also verified by XRD. The samples were run at the 2θ ranges from 5° to 50° C. The signals were acquired at a scanning rate of 0.02°/s at 30 kV and 10 mA measurement conditions. Graph 1000, provided in FIG. 10, compares the intensity (a.u.) versus 2θ (degrees) for GO 1002 and rGO 1004. The appearance of a peak at 24.96° in line 1004 indicates a low interlayer distance due to the elimination of oxygen-containing groups during reduction.

Figure 11:
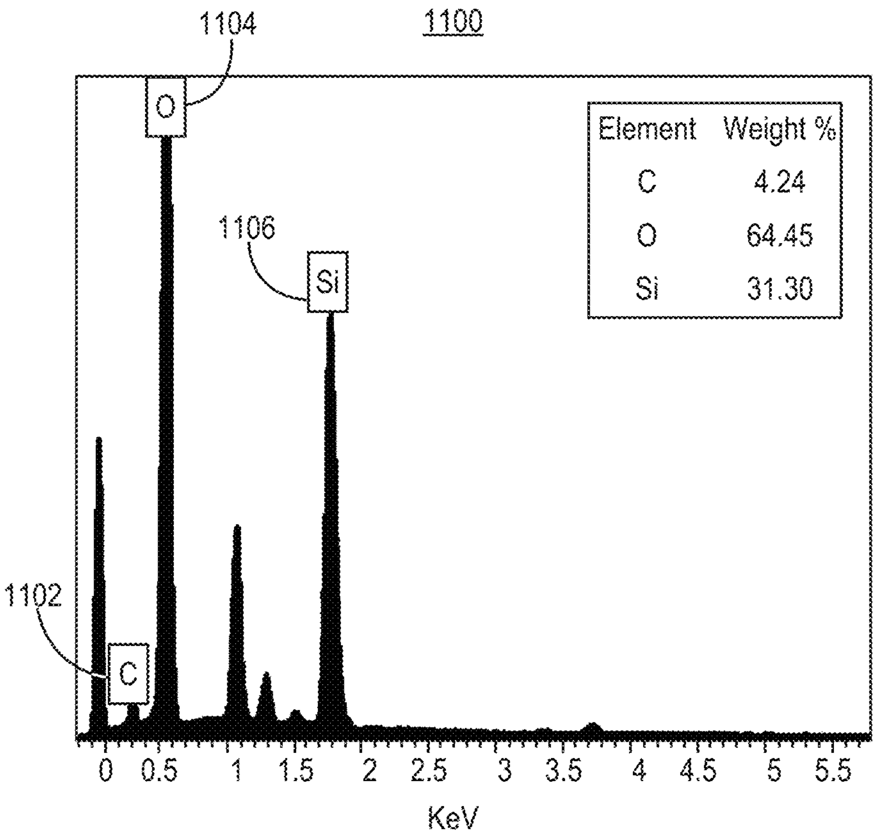
FIG. 11 illustrates a graph of spectra obtained by energy-dispersive X-ray analysis (EDX) of GO, according to some embodiments.
Figure 12:
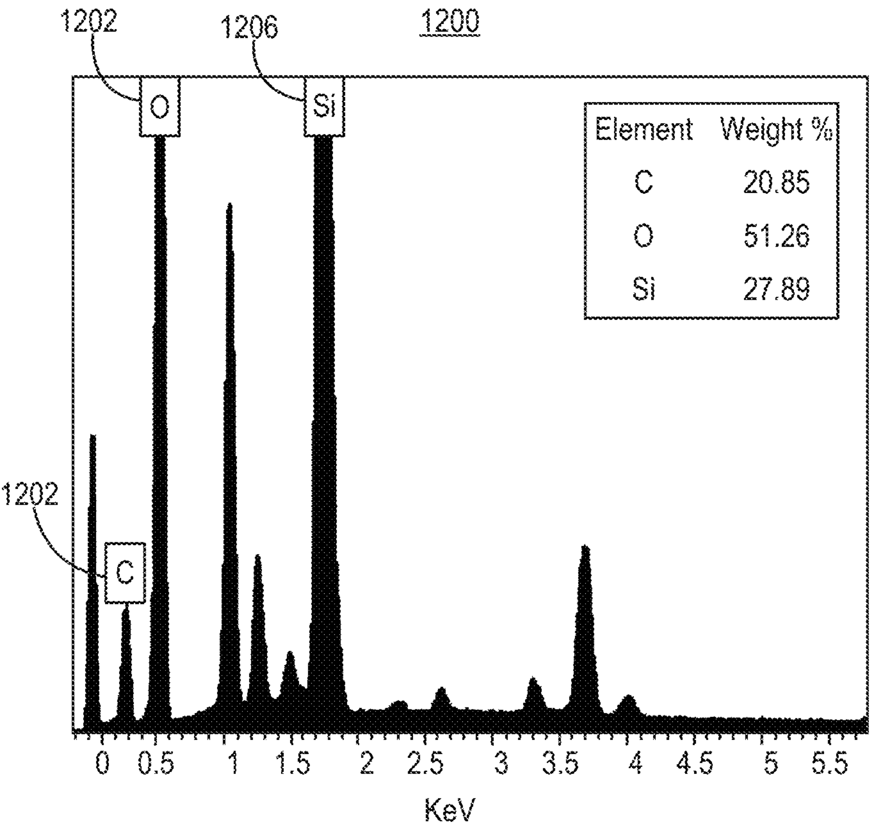
FIG. 12 illustrates an EDX spectra of rGO, according to some embodiments.

FIG. 11 and FIG. 12 illustrate experimental results from EDX analysis of GO, (graph 1100) and rGO (graph 1200). Graph 1100 includes peaks for carbon (C) 1102, oxygen (O) 1104, and silicon (Si) 1106. Similarly, graph 1200 includes peaks for carbon (C) 1202, oxygen (O) 1204, and silicon (Si)

1206. EDX analysis may be utilized to quantify the elimination of oxygen-containing groups. As shown in FIGS. 11 and 12, the weight percentage of oxygen atoms 1104, 1204 decreased from 64.6% to 51.3% after GO reduction.

Figure 13:
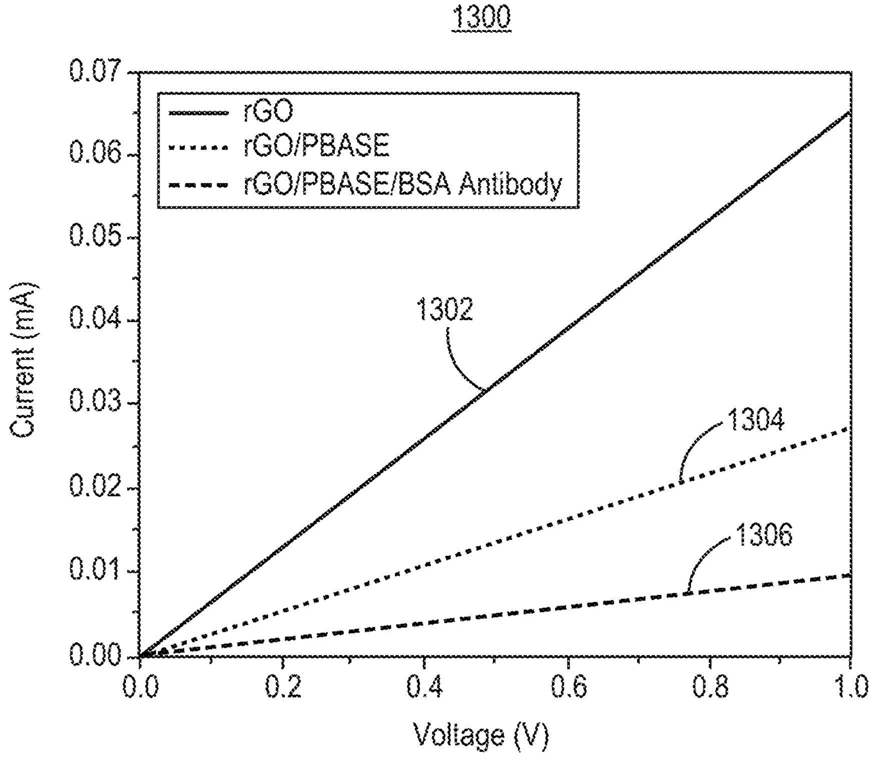
FIG. 13 illustrates electrical characterization of the rGO biosensor as shown in a graph of current-voltage curves.
Figure 14:
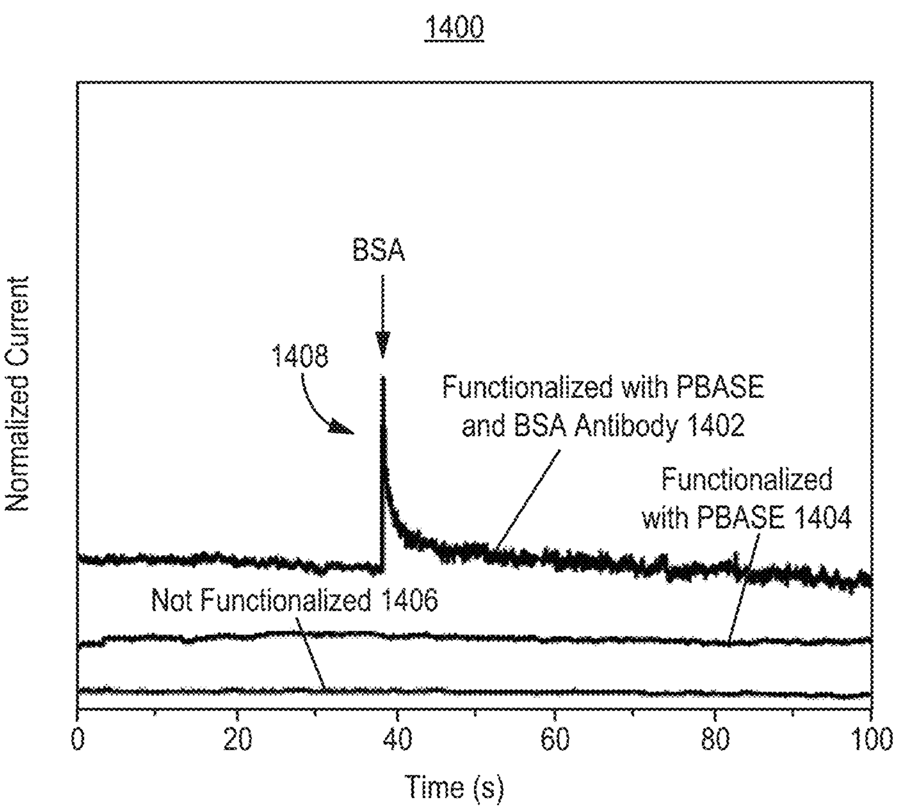
FIG. 14 illustrates graph showing the variation in current obtained after the introduction of BSA proteins at t=40 s after each surface modification step of method 200.

FIGS. 13-15 illustrate experimental results from the analysis of rGO surface functionalization with PBASE linker 140 and BSA antibodies 130. Graph 1300 in FIG. 13 provides voltage curves for rGO 1302, rGO/PBASE 1304, and rGO/PBASE/BSA antibody 1306. The voltage (V) varied from 0.0 to 1.0 V. As shown in FIG. 13, after PBASE functionalization and BSA antibody immobilization, the slope (dI/dV) decreased, indicating an increase in resistance in the rGO layer. An increase in resistance, associated with a decrease in the slope of (dI/dV), is observed after each step. A decrease in the slope correlates to the successful introduction of PBASE linker 140 and BSA antibodies 130.

Graph 1400 in FIG. 14 illustrates the results of real-time electrical measurements that were performed. A constant voltage of 0.0008V was applied and the current was measured at t=40 seconds after the introduction of BSA proteins to a non-functionalized surface 1406, a surface functionalized with PBASE linker 1404, and a surface functionalized with PBASE and BSA antibody 1402 (an antibody immobilized surface). Only the surface functionalized with PBASE and BSA antibody 1402 was observed to have a peak 1408. Thus, graph 1400 illustrates that the detection of BSA antigen was observed only when the surface was modified with linker 140 and antibody 130.

Figures 15A, 15B, 15C:
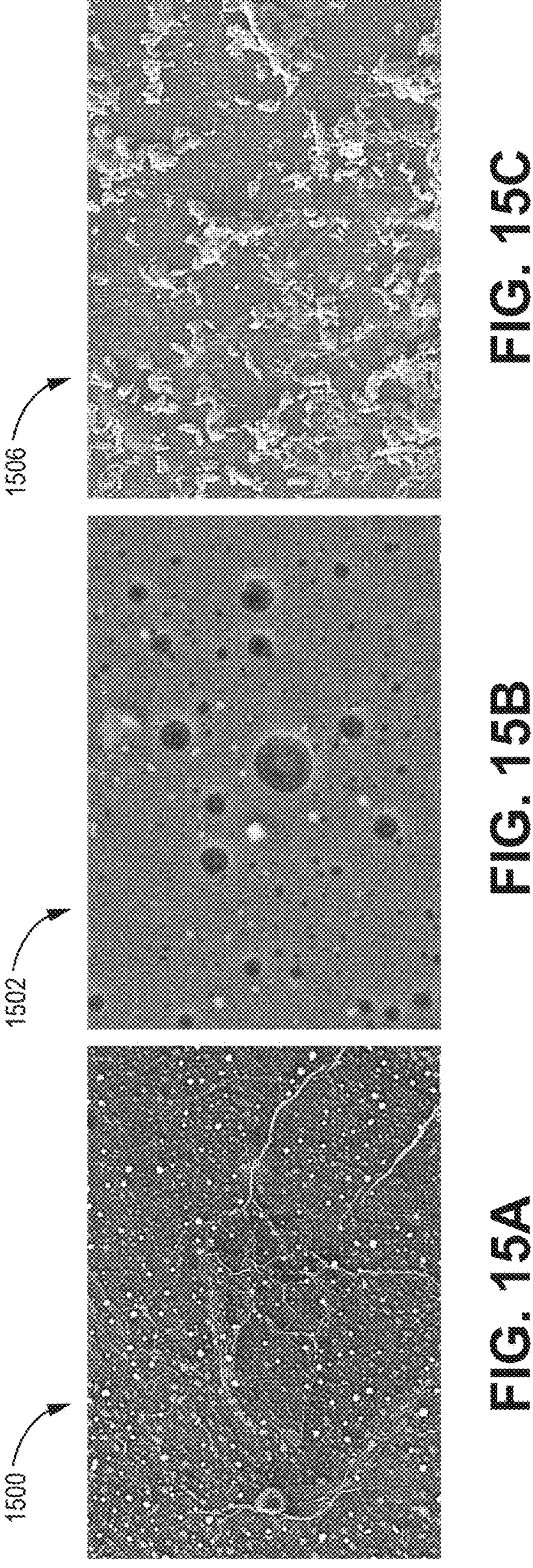
FIGS. 15A-C are scanning electron microscopy (SEM) micrographs obtained after each surface modification step of method 200, according to some embodiments.

FIGS. 15A-C respectively are a SEM micrograph 1500 of the surface of the rGO substrate 122, a SEM micrograph 1502 of the PBASE functionalized surface 124, and a SEM micrograph 1504 of the antibody immobilized surface 100. The SEM micrograph 1500 illustrates the wrinkled architecture of the surface of the rGO substrate 122. The SEM micrographs 1502 and 1504 respectively illustrate the surface changes that are seen after PBASE modification and after antibody immobilization.

Figure 16:
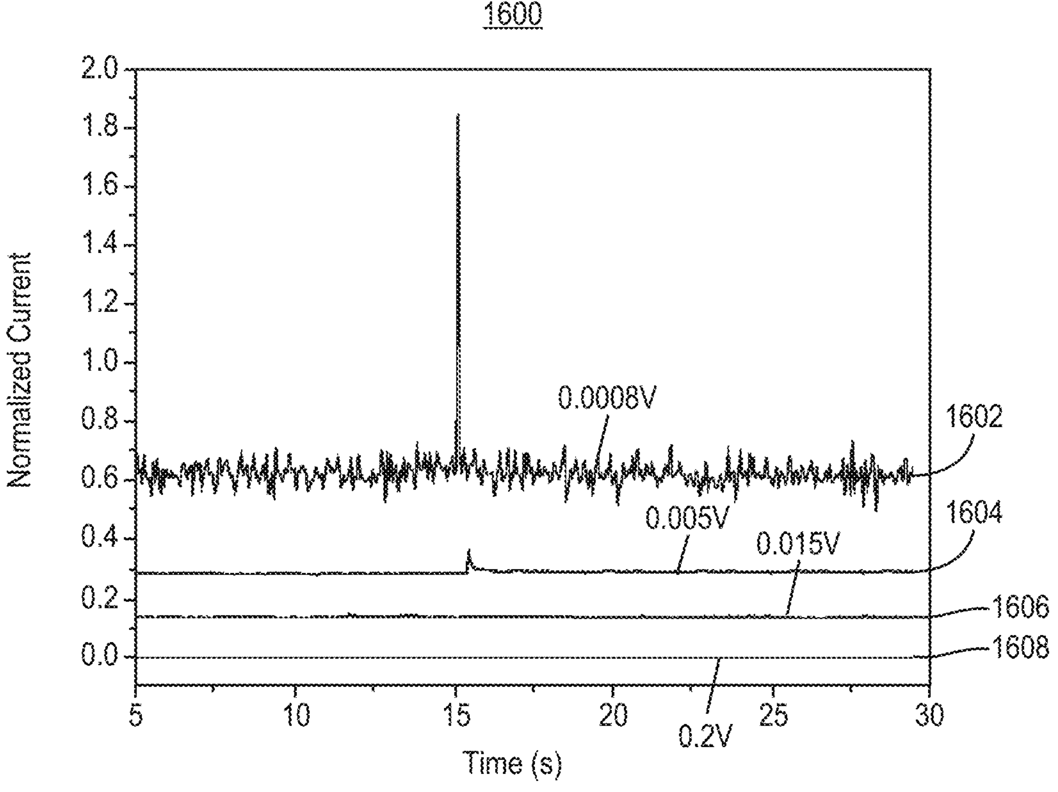
FIG. 16 illustrates a graph of electrical characterization of rGO biosensor detection at different applied voltages, according to some embodiments.

FIGS. 16-18 illustrate experimental results of analyses of the effect of the electric field on biosensor detection. Real-time electrical measurements were obtained by applying different constant voltages on the biosensor's functionalized surface, during which BSA protein was introduced. At different applied voltages, the performance of the biosensor concerning its detection capability was assessed through peak signals of normalized current, which imply successful antigen-antibody complexes, as shown in FIG. 16. Graph 1600 illustrates a curve 1602 for an applied voltage of 0.0008 V, a curve 1604 for an applied voltage of 0.005 V, a curve 1606 for an applied voltage of 0.015 V and a curve 1608 for an applied voltage of 0.2 V. No peaks were observed in curves 1608 and 1606 (0.2 V and 0.015 V) upon introducing the BSA protein while sharp peaks were observed in curves 1604 and 1602 (0.005 V and 0.0008 V). However, at 0.0008 V, curve 1602, the detection was associated with a much greater and more pronounced peak than for 0.005 V, curve 1604. These results show noticeable changes in the biosensor detection of BSA at various electric field strengths with detection most prominent at 0.0008 V but still possible at 0.005 V. However, applied voltages lower than 0.005 V and greater than 0.015 V resulted in a loss of the biosensor's ability to detect BSA. Without being bound by theory, when BSA is in contact with the biosensor 100 the rGO layer 120 becomes more n-doped. Therefore, antigen-antibody interactions are translated into increases in the initial current value at positive applied voltage values. This is reflected in the positive current peaks, as seen upon the introduction of BSA proteins. The electrical characterization illustrated in graph 1600 confirms that biological functions of the BSA protein are impacted at sufficiently high electric field conditions.

Figures 17A, 17B, 17C, 17D, 17E:
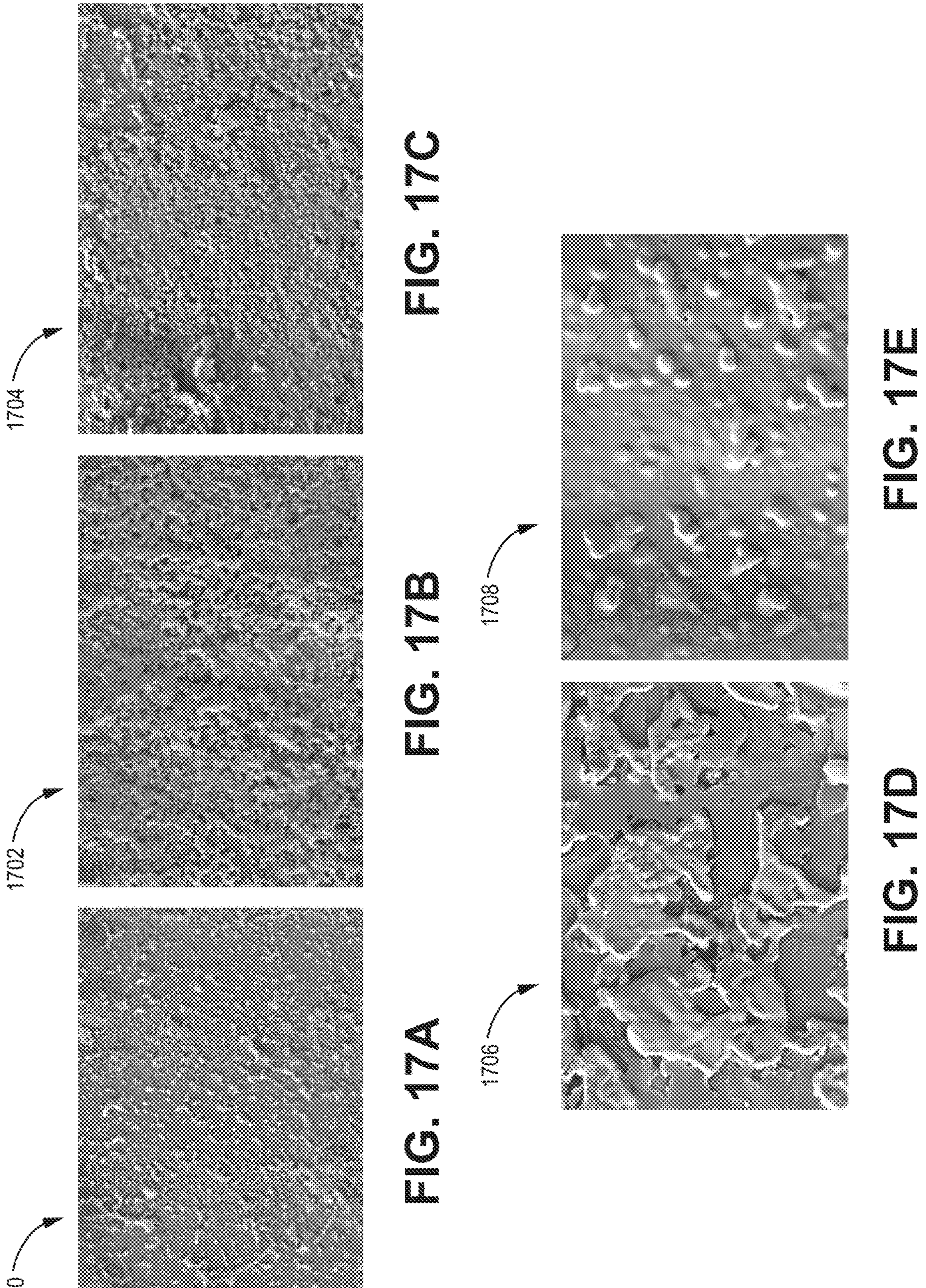
FIGS. 17A-E are low magnification (×3, 700) SEM images of the biosensor surface at applied voltages of (A) 0V, (B) 0.0008 V, (C) 0.005 V, (D) 0.015 V, and (E) 0.2 V, according to some embodiments.
Figures 18A, 18B, 18C, 18D, 18E:
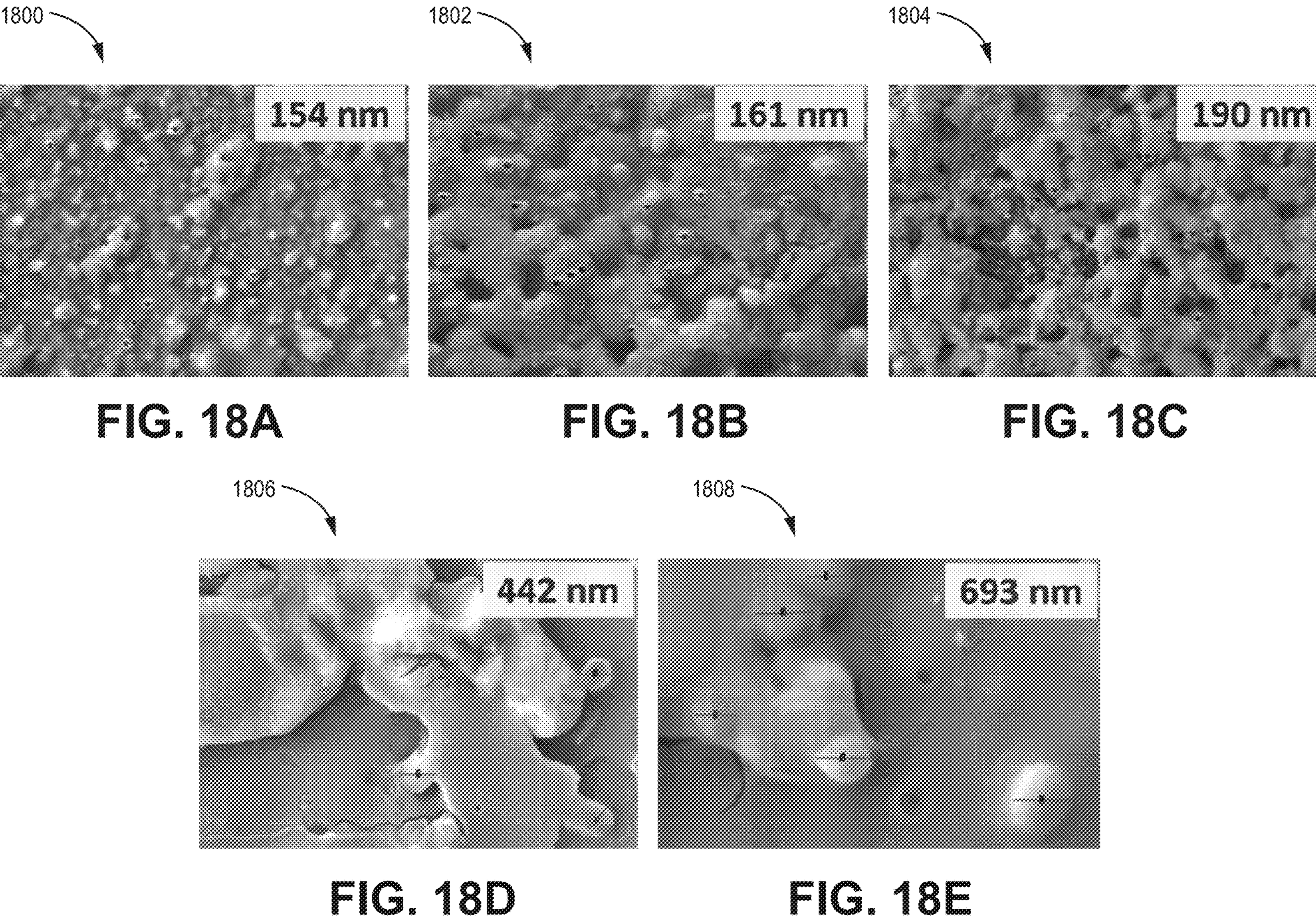
FIGS. 18A-E are high magnification (×19,000) SEM images of the biosensor surface at applied voltages of (A) 0V, (B) 0.0008 V, (C) 0.005 V, (D) 0.015 V, and (E) 0.2 V, according to some embodiments.

SEM and C-AFM imaging analysis was performed to investigate this observation. Before morphological analysis, the surface of the biosensor 100 was coated with a 7 nm thick palladium layer to maximize conductivity. For SEM imaging, a constant voltage was applied to the biosensor samples beforehand for a sufficient duration. FIGS. 17A-E are low magnification (×3,700) SEM micrographs 1700-1708 of the surface of the biosensor 100 and FIGS. 18A-E are high magnification (×19,000) SEM images 1800-1808 of the surface of the biosensor 100 at applied voltages of (A) 0 V, (B) 0.0008 V, (C) 0.005 V, (D) 0.015 V, (E) 0.2 V. The SEM micrographs 1700-1704 for 0 V, 0.0008 V, and 0.005 V show dispersed layers of BSA proteins across the biosensor surface. The dispersion of BSA proteins differed slightly as the electric field increased. For example, in the range of 0 to 0.005 V, the surface showed slightly less BSA proteins at the higher end (i.e., 0.005 V) and more dispersion of BSA proteins at the lower end (0 V control). When viewed at a much higher magnification, the same samples showed BSA proteins with sizes ranging from 154 to 190 nm as the applied voltage increased from 0 to 0.005 V (see FIGS. 18A-C). The same trend was not observed for biosensors with an applied constant voltage greater than 0.015 V. At low magnification, the SEM micrographs in FIGS. 17A-E showed significant changes in surface morphology. The aggregation of BSA proteins is evident at an applied of 0.015 V, as shown in FIGS. 17D and 18D. Besides prominent aggregation, BSA protein size significantly increased from 190 to 442 nm for applied voltages of 0.005 and 0.015 V, respectively. When the applied voltage exceeded 0.015 V, aggregation was still observed with a protein size of 693 nm at 0.2 V, as shown in FIGS. 17E and 18E.

Figure 19:
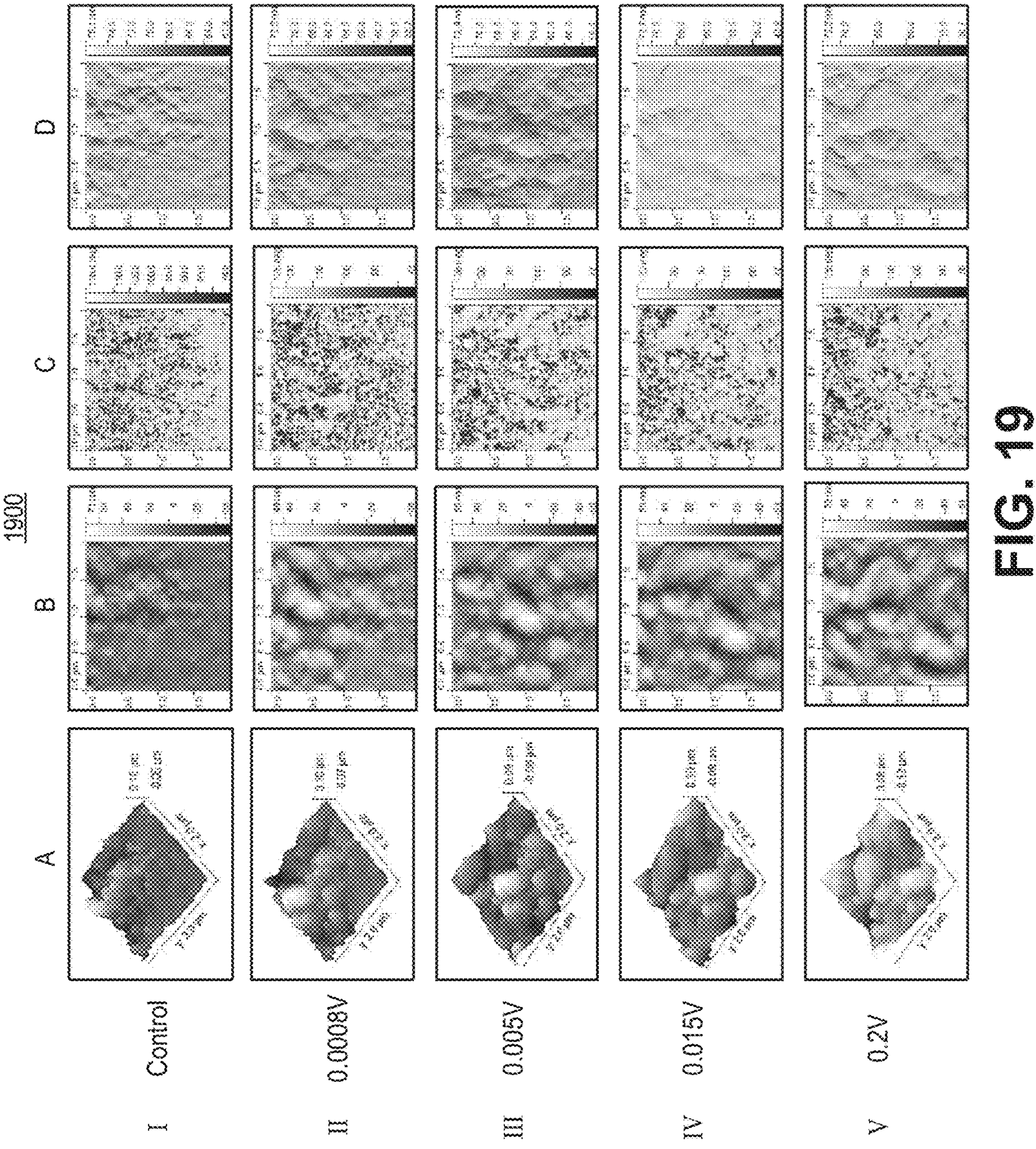
FIGS. 19A-D are conductive atomic force microscopy (C-AFM) images showing (A) 3D images, (B) topography, (C) phase, and (D) amplitude of the biosensor at different applied voltages (control, 0.0008 V, 0.005 V, 0.015 V, and 0.2 V), according to some embodiments.

C-AFM analysis of the topography of the biosensor 100 as a function of electric field was also conducted. The analysis utilized a gold (AU) conductive tip with an apex radius of 30 nm. A constant voltage was applied on the biosensor surface for 10 minutes, while the Au tip was brought into contact with the area of interest. An AFM system, placed in a closed chamber, was utilized to apply an electric field. The voltage was applied to the surface of the biosensor 100 while the Au tip was kept at the ground. After the voltage was applied, the topography of the biosensor was explored using AC-air topography mode. Constant voltages were applied consecutively, with the topography being analyzed immediately after each voltage application to ensure that the topography results were correlated with the same area of the biosensor. Additionally, for consistency, an electric field was applied for the same duration, 10 minutes, for both SEM and AFM characterization. FIG. 19 provides C-AFM images showing (A) three-dimensional (3D) image, (B) topography, (C) phase, and (D) amplitude of the biosensor 100 at (I) 0 V control, (II) 0.0008 V, (III) 0.005 V, (IV) 0.015 V, and (V) 0.2 V. For consistency, the images in FIG. 19 are based on the same 2×2 $cm^2$ area of the biosensor surface and all comparisons were made to the control images (0 V). The 3D images (images IA-VA) show an apparent increase in the particle size of BSA (i.e., particle agglomeration) as the voltage increases. The changes in the color observed in phase images (IC-VC) and topographic images (IB-VB) distinguish between the different materials present on the overall surface, which are the biosensor composite and BSA proteins. The surface appears to be uniform at 0.0008 V, above which phase images IIIC-VC indicate the dominant aggregating phase of BSA on the surface. Moreover, amplitude images ID-VD confirm the BSA proteins' growing size and aggregation as the applied voltage increases. This is also reflected in the obtained RMS values.

The SEM micrographs and C-AFM assessments suggest a sudden rise in protein size and aggregation above an applied voltage of 0.005 V. Under strong electric fields, the tertiary structure of proteins tends to unfold and aggregate, as shown in FIGS. 17-18. The results are also consistent with the electric field inducing changes in the intra-protein hydrogen bonds, which contribute to the overall weakened stability of the BSA structure.

Table 1 provides surface roughness values obtained through C-AFM assessments in different electric fields.

TABLE 1

Root Mean Square (RMS) of a surface at different applied voltages

| Applied Voltage (V) | RMS (nm) |
|---|---|
| 0 | 17.32 |
| 0.0008 | 24.58 |
| 0.005 | 24.78 |
| 0.015 | 26.91 |
| 0.2 | 31.95 |

The increase in RMS from 17.32 at 0 V to around 25 nm at 0.0008 and 0.005 V. indicates minor changes in surface characteristics. The dramatic increase in the RMS value at 0.015 V to 0.2 V conforms the results observed with SEM and C-AFM, which indicated that the BSA protein slightly increases in size and aggregates at these voltages.

Figure 20:
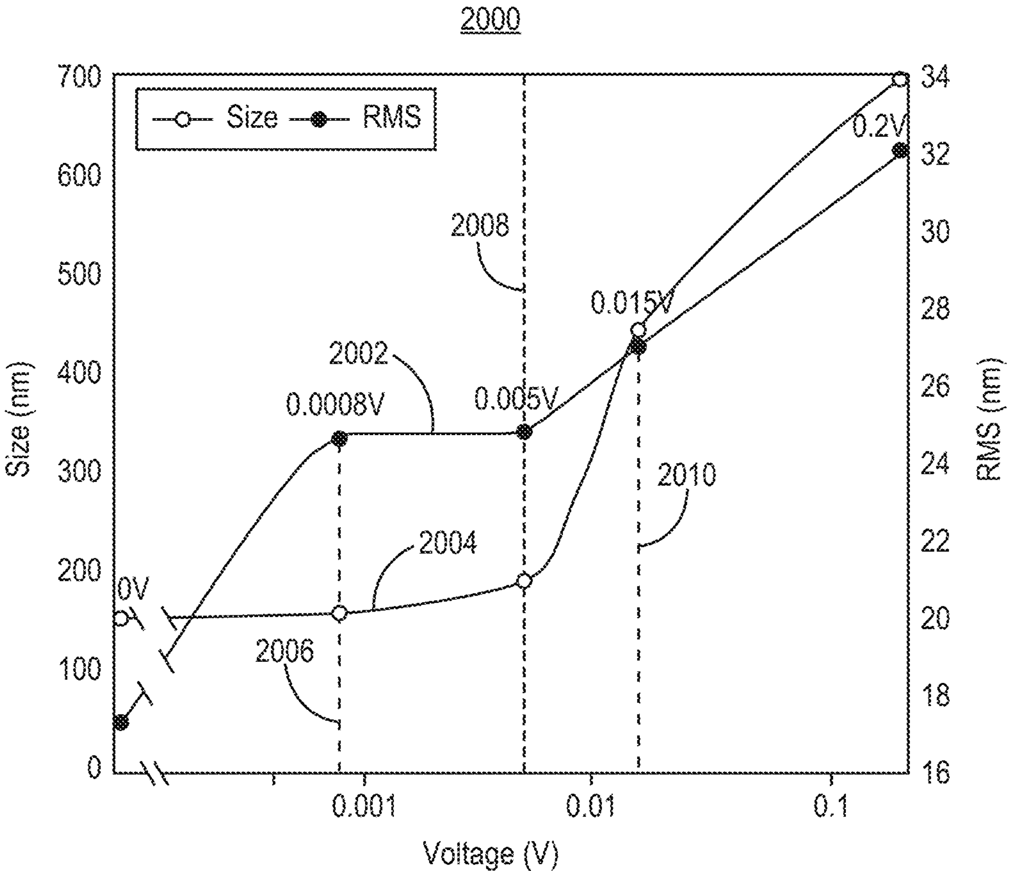
FIG. 20 illustrates a graph showing changes in bovine serum albumin (BSA) protein size (left axis) and root mean square (RMS) (right axis) with varying electric field strengths (log scale), according to some embodiments.

FIG. 20 is a graph 2000 comparing the trends in BSA protein size (left axis), curve 2004, with surface roughness (RMS) (right axis), curve 2002, against applied voltage via a semi-log plot. Line 2006 is at 0.0008 V, line 2008 is at 0.005 V and line 2010 is at 0.015 V. The BSA size changes slightly before and up to 0.005 V (line 2008), whereas the surface roughness is lower at 0 V than at 0.0008 V (line 2006), and 0.005 V (line 2008). Nevertheless, both size and surface roughness have approximately similar values at the latter voltages, indicating a low impact of the electric field. Furthermore, an applied voltage above 0.005 V, e.g., 0.015 V (line 2010), causes significant changes to the surface of the biosensor 100, as evidence by the massive increase in size and surface roughness plots, marking 0.005 V as the breakthrough value. Thus, when applied voltages greater than 0.005 V are applied to the biosensor 100, there is a decrease in the detection capacity of the biosensor 100 and a decrease in the protein structural conformations of the antigen-antibody complexes.

Biosensor Performance—Response to BSA Protein

Figures 21A, 21B:
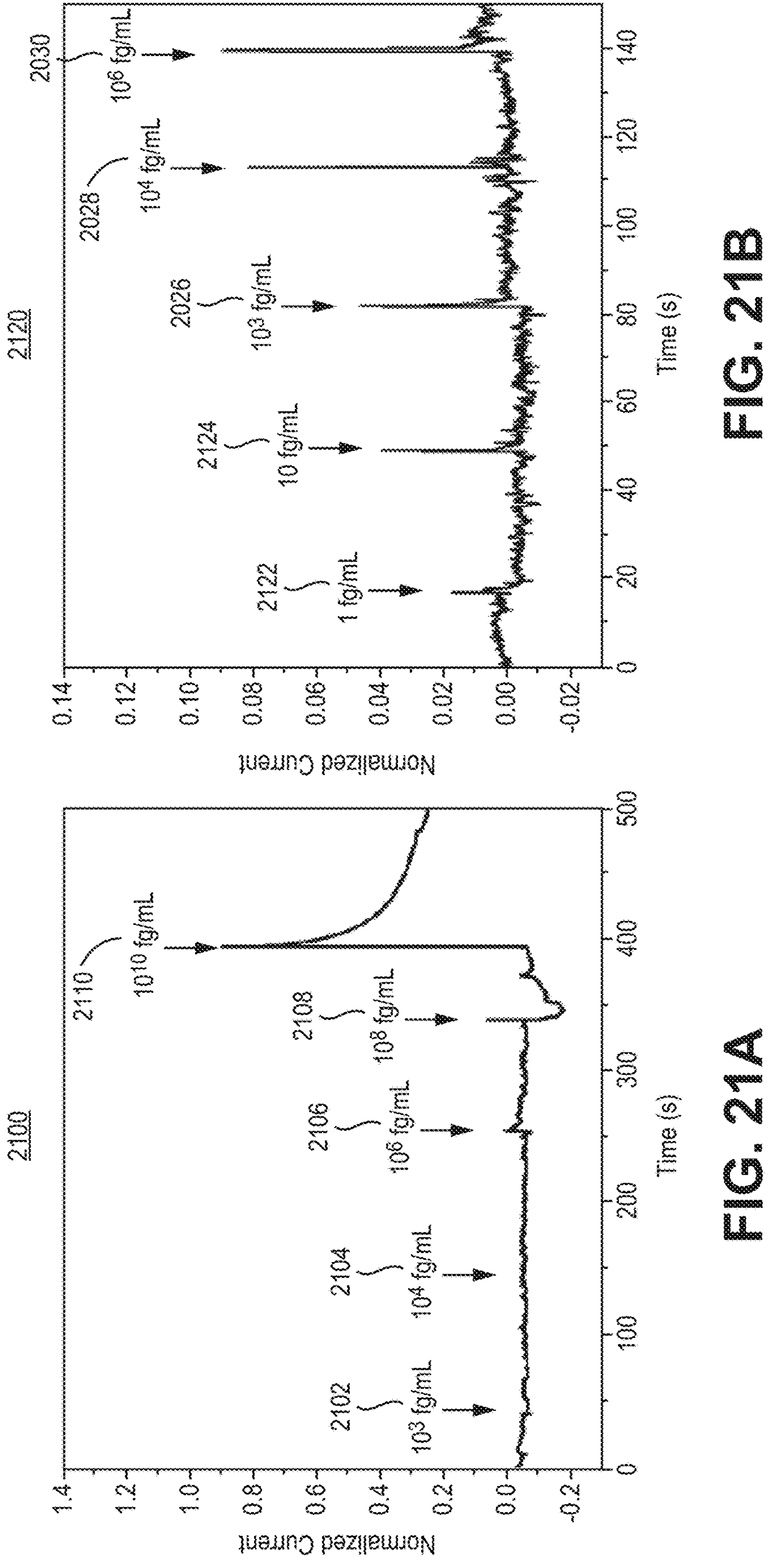
FIGS. 21A-B illustrate graphs showing real-time response of the biosensor at an applied voltage of (A) 0.2 V and (B) 0.0008 V, according to some embodiments.

FIGS. 21A and 21B are graphs 2100, 2120 of the real-time response of the biosensor 100 to BSA proteins at an applied voltage of (A) 0.2 V and (B) 0.0008 V. In graph 2100, peak 2102 represents $10^3$ fg/mL, peak 2104 represents $10^4$ fg/mL, peak 2106 represents $10^6$ fg/mL, peak 2108 represents $10^8$ fg/ml, and peak 2110 represents $10^{10}$ fg/mL. In graph 2120, peak 2122 represents 1 fg/mL, peak 2124 represents 10 fg/mL, peak 2126 represents $10^3$ fg/mL, peak 2128 represents $10^4$ fg/mL, and peak 2130 represents $10^6$ fg/mL. Graph 2100 illustrates that at a fixed voltage of 0.2V, the limit of detection (LOD) for BSA proteins by the biosensor 100 was observed to be at $10^6$ fg/mL (peak 2106). For these experiments, the LOD is the minimum concentration at which the biosensor 100 started to show a response. Graph 2120 illustrates that at a fixed voltage of 0.0008 V, the LOD of the biosensor 100 was observed to be 1 fg/mL. Thus, the LOD of the biosensor 100 was over 100 fold lower at the fixed voltage of 0.0008 V than at a fixed voltage of 0.2 V.

Figure 22:
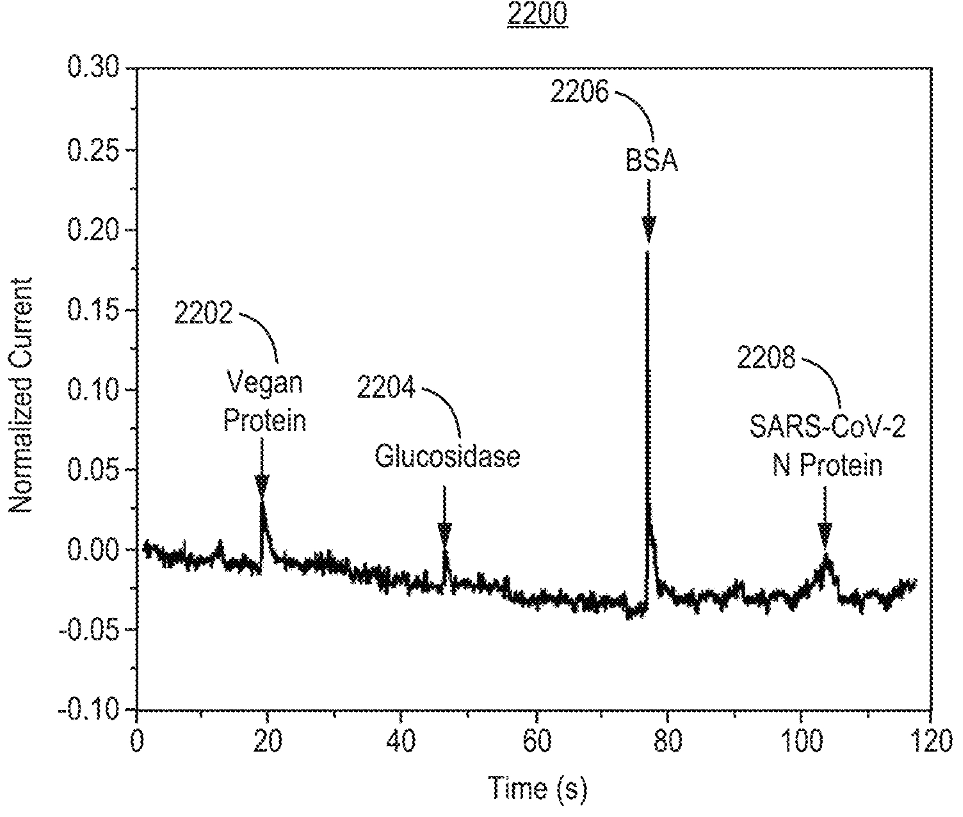
FIG. 22 illustrates a graph showing real time response of the biosensor at an applied voltage of 0.0008 V against non-specific proteins.

To investigate the specificity of the biosensor to BSA, three non-specific target proteins were used. As illustrated by graph 2200 of FIG. 22, the biosensor 100 did not show any response upon exposure to commercial vegan protein 2202, glucosidase 2204, and SARS-CoV-2 N protein 2208 but did respond to BSA protein 2206. The lack of time-dependent peaks in the current verifies that these non-specific proteins do not bind to the surface-immobilized BSA antibodies. This implies that the biosensor 100 is both highly sensitive and highly selective.

Figure 23:
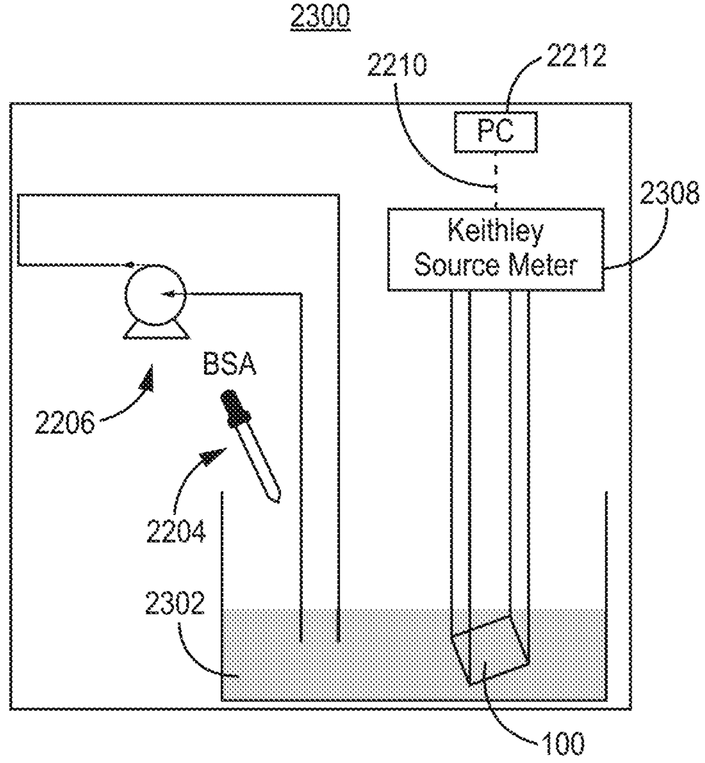
FIG. 23 illustrates a schematic view of a detection system to test the performance of the biosensor in conditions simulating wastewater, according to some embodiments.
Figure 24:
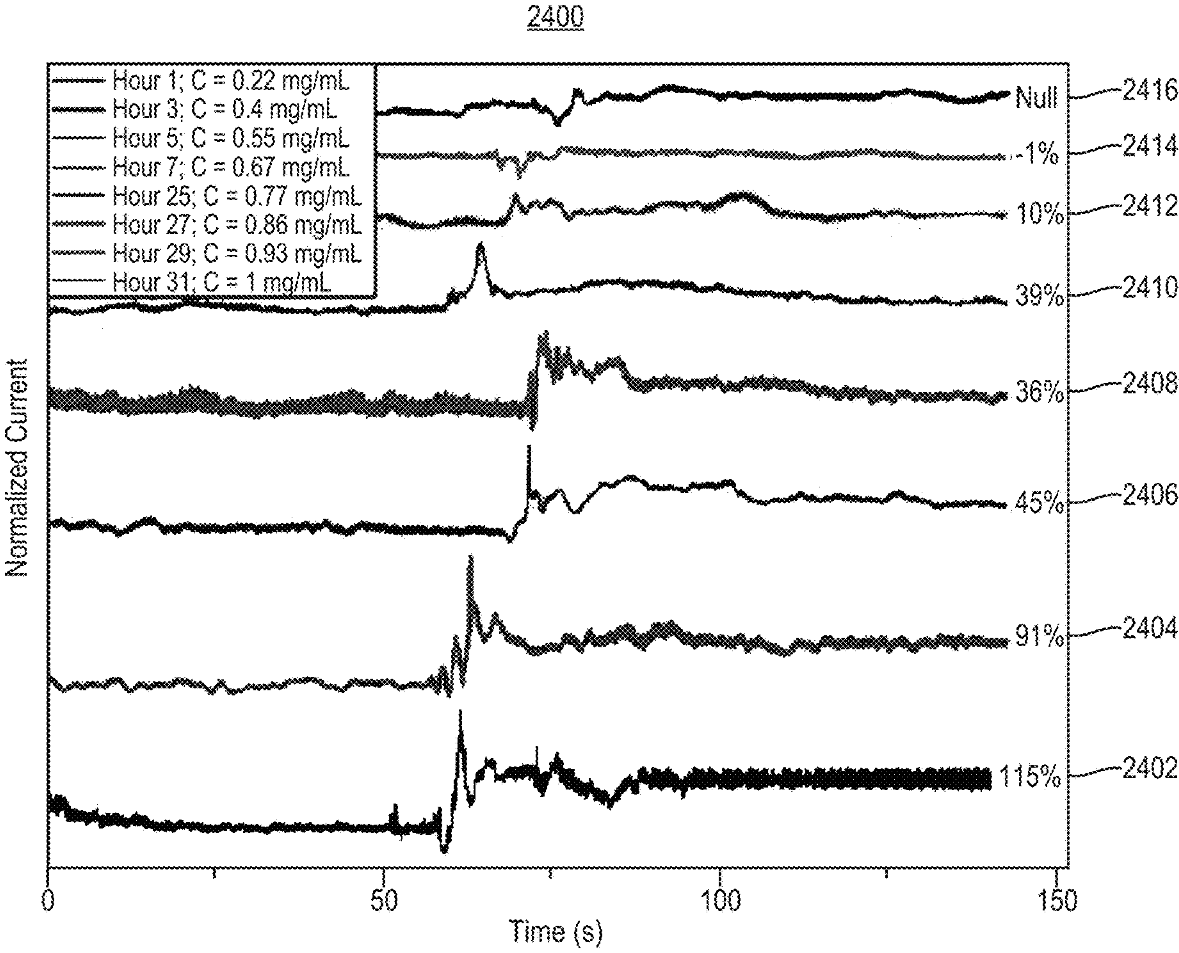
FIG. 24 illustrates a graph of normalized current upon consecutive additions of BSA proteins, according to some embodiments.
Figure 25:
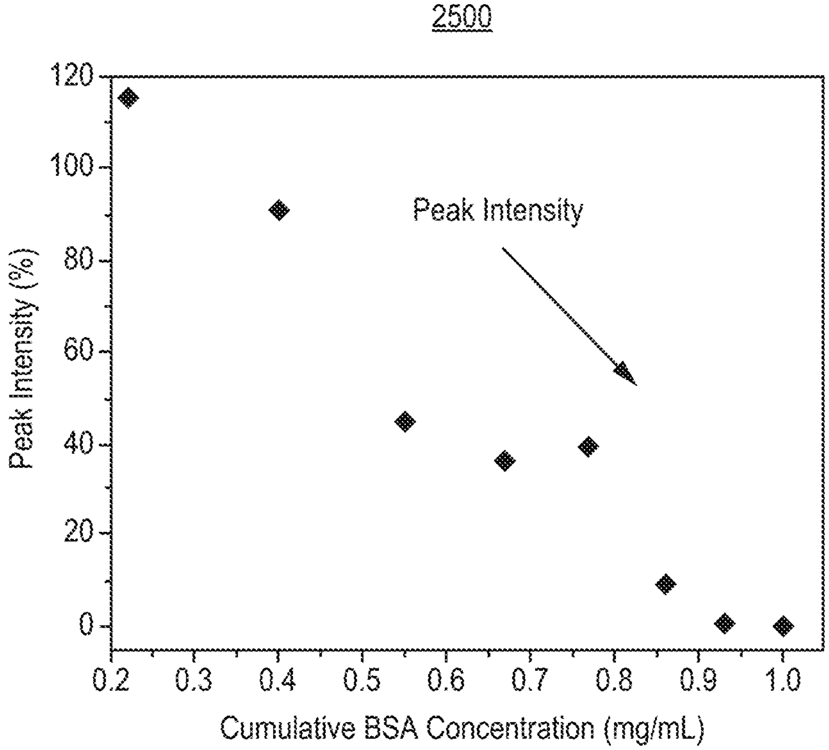
FIG. 25 illustrates a graph of peak intensity (%) and cumulative BSA concentration (mg/mL) showing an association between peak intensity and cumulative BSA concentration, according to some embodiments.

The performance of the biosensor 100 in flowing water conditions was assessed. FIG. 23 is a schematic diagram of the experimental system 2300. The system 2300 includes a biosensor 100, with isolated metal contacts, positioned in a bath 2302 of DI water, the biosensor 100 is coupled to a Keithley source meter 2308, flowing water conditions in the bath 2302 were provided by a peristaltic pump 2306 configured to circulate the DI water at a flowrate of 6.7 L/h in a closed loop, and the Keithley source meter 2308 is in communication with a PC 2312. In each run, 50 mL of 2 mg/ml BSA protein solution 2304 was added to the bath 2302. Real time current measurements under flowing water conditions were recorded upon the introduction of BSA protein solution 2304 to the bath 2302. Graph 2400 provided in FIG. 24 illustrates the measured normalized current upon consecutive additions of BSA protein. Although water flow was observed to create a certain noise level in the measured current, clear current peaks were generated, indicating that the sensitivity of the biosensor 100 is maintained under conditions mimicking those of wastewater flow. Additionally, the degradation of the biosensor's peak intensity was clearly associated with the increase in cumulative BSA concentration. Thus, the performance of the biosensor 100 is maintained at cumulative concentrations less than 1 mg/mL, where it approaches saturation, as reflected by graph 2500 of FIG. 25.

Biosensor Performance—Response to SARS-CoV-2 S1 Protein

Turning to FIGS. 26-28, an analysis of the performance of a rGO biosensor 100 with a binding affinity to the SARS-CoV-2 S1 protein was conducted.

Figures 26A, 26B, 26C, 26D:
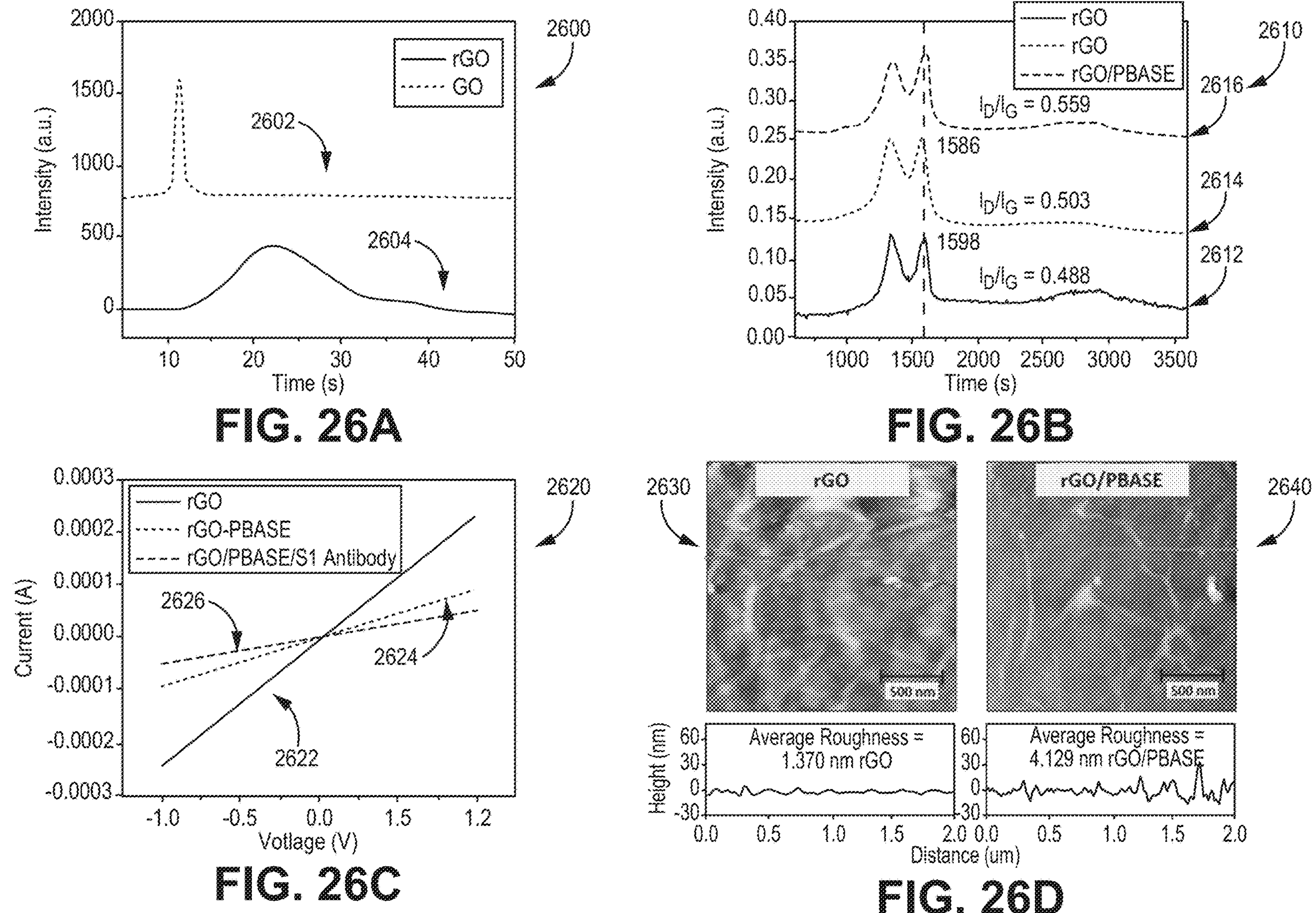
FIGS. 26A-D illustrate the analytical and electrical characterization of the rGO biosensor, according to some embodiments.

GO deposition, reduction, and functionalization was characterized using XRD (graph 2600 of FIG. 26A), Raman spectroscopy (graph 2610 of FIG. 26B), and AFM (graphs 2630 and 2640 of FIG. 26D). Graph 2600 illustrates the XRD patterns of GO 2602, and rGO 2604 (FIG. 26A). The XRD pattern of GO 2602 exhibits a sharp peak at 2θ=11.52°, while after the reduction, the peak is shifted to 2θ=22.1°. In GO, the peak is sharp, while a broader peak is observed for rGO, which implies that the crystal phase (002) is randomly arranged in rGO compared to a high crystallization structure in GO. Moreover, the observed shift is a result of a reduction in the interlayer distance within GO layers, indicating the elimination of oxygen-containing groups. The electrical stability of the rGO biosensor 100 was verified by sweeping the voltage from −1 to 1 V in 101 steps and obtaining a constant resistance.

Graph 2610 illustrates the Raman spectra of GO 2612, rGO 2614, and rGO/PBASE 2616 (FIG. 26B). Each sample displayed two prominent peaks—one detected at ~1345 $cm^{-1}$ and another detected at ~1597 $cm^{-1}$ corresponding to the D and G bands, respectively. These two peaks correspond to two fundamental vibrations—where the peak corresponding to the D band symbolizes the disorder and the peak corresponding to the G band correlates to the in-plane stretching of the C—C bond. In addition to XRD, the reduction of GO was verified via Raman spectra with a clear shift in the G-band from 1598 to 1686 $cm^{-1}$. Raman spectra also showed an increase in defects after reduction and PBASE functionalization. It is noted that the chances of desorption are significantly hindered by such tight binding. The increase in defects upon PBASE functionalization is characterized by the peak ratio between the intensity of the D peak and the G peak ($I_D/I_G$). The peak ratio is used as a common index to determine the density of defects. The reduction in GO to rGO increases the number of disordered phases translated by a larger $I_D/I_G$ for rGO. Moreover, rGO functionalization results in an increase in defects as with chemical vapor deposition (CVD) graphene. This is demonstrated by the results obtained with $I_D/I_G$ increasing from 0.488 to 0.559 when moving from GO to rGO/PBASE, as shown in FIG. 26B, where a pyrene group of PBASE is bonded to the surface of rGO, resulting in some additional disorder. Furthermore, the graphs 2630 and 2640 illustrated in FIG. 26D reveal that the surface roughness of rGO, extracted from the AFM topography roughness surface analysis, increased significantly from 1.370 to 4.129 nm with PBASE functionalization.

FIG. 26C illustrates a graph 2602 of current-voltage (I-V) curves for rGO 2622, rGO/PBASE 2624, and the rGO biosensor 2626 in a range from −1 to +1 V. Curves 2622 and 2624 illustrate the current observed before attachment of the S1 antibody. Curve 2626 illustrates the current observed for the rGO biosensor 100. An increase in resistance, associated with a decrease in the slope of (dI/dV), is observed after each step. This increase in resistance confirms the successful introduction of the S1 antibody.

Figures 27A, 27B, 27C, 27D:
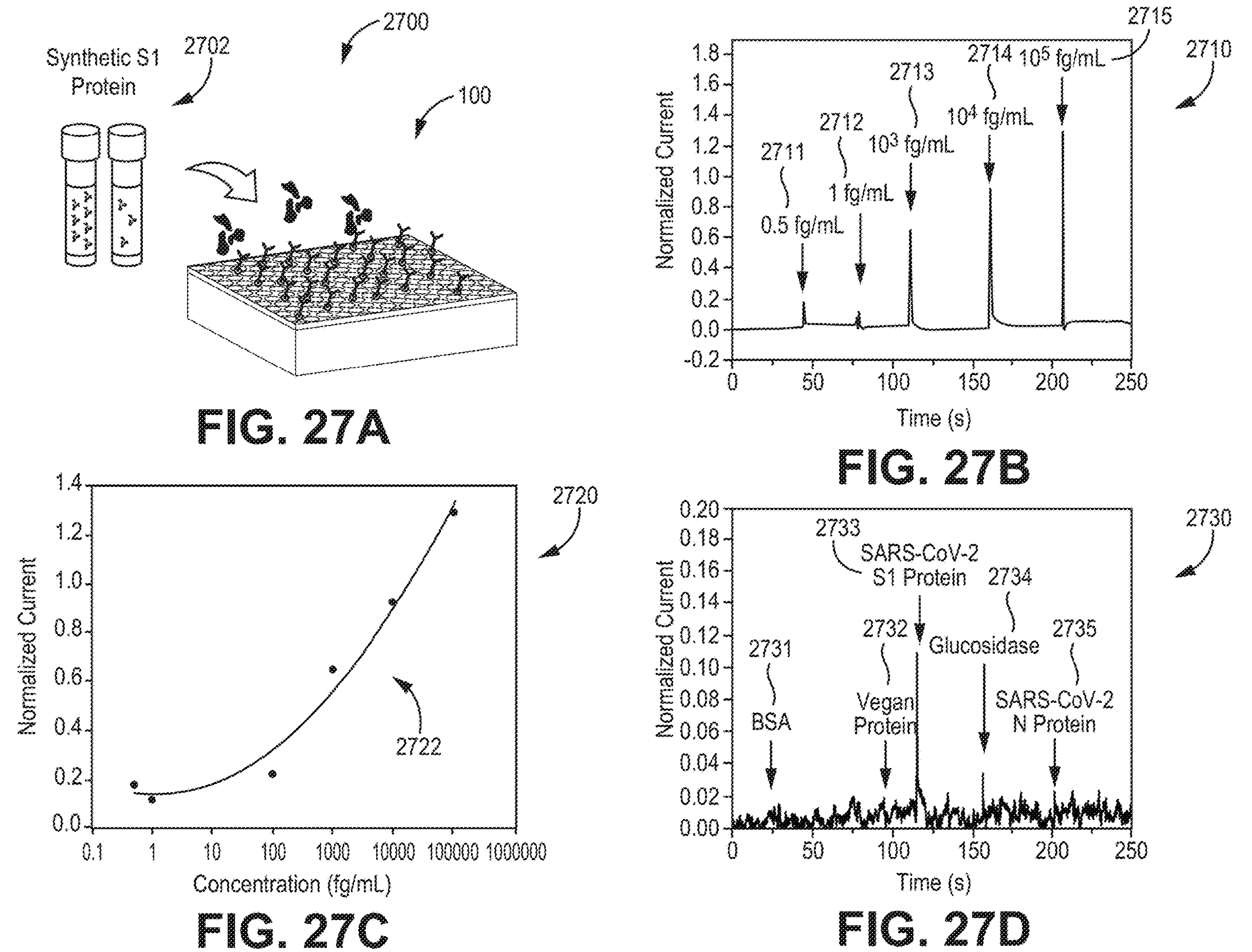
FIGS. 27A-D illustrate the response of the rGO biosensor to the SARS-CoV-2 S1 protein.

FIG. 27A is an illustration of a detection system 2700 with the biosensor 100 exposed to a sample 2702 of the SARS-CoV-2 S1 protein. Since the receptor-binding domain (RBD) in the S1 protein is positively charged, a constant voltage of −0.8 mV was applied during the testing. Graph 2710 and graph 2720, provided in FIGS. 27B and 27C respectively, illustrate the real-time dynamic response of the rGO biosensor 100 to increasing concentrations of S1 protein. Graph 2710 illustrates the changes in normalized current with time with the addition of different concentrations of S1 protein in PBS (FIG. 25B). Peak 2711 represents 0.5 fg/mL, peak 2712 represents 1 fg/mL, peak 2713 represents $10^3$ fg/mL, peak 2714 represents $10^4$ fg/ML and peak 2715 represents $10^5$ fg/mL. A sharp increase in the current values suggests binding of the S1 protein to the immobilized S1 antibody, after which the value stabilized. The SARS-CoV-2 S1 protein in PBS was detected by the rGO biosensor 100 at concentrations as low as 0.5 fg/mL. Graph 2720 illustrates that the rGO biosensor 100 showed a response to each concentration greater than 0.5 fg/mL, with a trend as shown by curve 2722 (FIG. 27C). Graphs 2710 and 2720 both illustrate that as the concentration of the S1 protein increases, the sharp peak for the current value increases. Real-time current measurements were also carried out using S1 protein concentrations below the LOD, but no changes in the current values were observed. These results indicate that the rGO biosensor 100 is highly sensitive with a lower LOD than other SARS-CoV-2 detection methods.

FIG. 27D illustrates a graph 2730 of the response of the rGO biosensor 100 to non-specific interfering proteins. To test the specificity of the rGO biosensor 100, 20 μL of 0.3 mg/mL, of BSA protein 2731, commercial vegan protein 2732, SARS-CoV-2 S1 protein 2733, glucosidase enzyme 2734, and SARS-CoV-2 N protein 2735, were injected consecutively into the test pool while measuring real-time current. The rGO biosensor 100 did not generate any response (i.e., the current remained unchanged) after it was exposed to these non-specific proteins while a sharp current peak was observed upon the introduction of S1 protein, its target analyte. These results confirmed the specificity of the rGO biosensor 100. A response time, measured as the interval between the initial stable current and the peak current value, was determined to be around 240 is.

Table 2 provides data comparing the performance of the biosensor 100 to polymerase chain reaction (PCR) and CT value (quantification cycle of the PCR) to detect SARS-CoV-2 in nasopharyngeal clinical samples. Testing methodology included: 1) collecting nasopharyngeal swabs; 2) RNA extraction of the swab sample to obtain the CT value; 3) reducing viscosity of the nasopharyngeal samples by diluting the swab sample in PBS; 4) applying 10 μl of the diluted sample to the biosensor 100; and 5) collecting electrical current readings in real time where the generation of a peak upon introduction indicates a positive sample and the absence of a peak indicates a negative sample.

TABLE 2

Performance Assessment of the Biosensor with Clinical Samples

| Sample ID | Collection Date | Gender | Age | Collection liquid | PCR results | CT value | Sensor Results |
|---|---|---|---|---|---|---|---|
| KU-COVID-TESTING-13202 | 4 Jul. 2022 | F | 46 | Transparent | Negative | NA | Not detected |
| KU-COVID-TESTING-13181 | 27 Jun. 2022 | F | 22 | Transparent | Negative | NA | Not detected |
| KU-COVID-TESTING-13236 | 12 Jul. 2022 | F | 55 | Transparent | Negative | NA | Not detected |
| KU-COVID-TESTING-13237 | 12 Jul. 2022 | M | 57 | Transparent | Negative | NA | Not detected |
| KU-COVID-TESTING-13235 | 12 Jul. 2022 | F | 31 | Transparent | Negative | NA | Not detected |
| KU-COVID-TESTING-13217 | 4 Jul. 2022 | F | 20 | Transparent | Negative | NA | Not detected |
| KU-COVID-TESTING-13230 | 4 Jul. 2022 | M | 21 | Transparent | Negative | NA | Not detected |
| KU-COVID-TESTING-13234 | 6 Jul. 2022 | M | 47 | Transparent | Positive | 36 | Detected |

TABLE 2-continued

Performance Assessment of the Biosensor with Clinical Samples

| Sample ID | Collection Date | Gender | Age | Collection liquid | PCR results | CT value | Sensor Results |
|---|---|---|---|---|---|---|---|
| KU-COVID-TESTING-13184 | 30 Jun. 2022 | M | 30 | Transparent | Positive | 22 | Detected |
| DOH-BUR-0000692845001-COVID-13879 | 29 Jun. 2022 | n/a | n/a | Pink | Positive | 16 | Detected |
| DOH-YAS-607269318-COVID-13787 | 21 Jun. 2022 | n/a | n/a | Pink | Positive | 24 | Detected |
| KU-COVID-TESTING-13228 | 4 Jul. 2022 | F | 31 | Transparent | Positive | 16 | Detected |
| DOH-PHD-1222932522-COVID-13897 | 29 Jun. 2022 | n/a | n/a | Pink | Positive | 24 | Detected |
| DOH-PHD-99902580302-COVID-13898 | 29 Jun. 2022 | n/a | n/a | Pink | Positive | 36 | Detected |
| DOH-PHD-99902580689-COVID-13899 | 29 Jun. 2022 | n/a | n/a | Pink | Positive | 27 | Detected |
| DOH-PHD-99902580896-COVID-13900 | 29 Jun. 2022 | n/a | n/a | Pink | Positive | 28 | Detected |
| DOH-PHD-99902581245-COVID-13901 | 29 Jun. 2022 | n/a | n/a | Pink | Positive | 22 | Detected |
| KU-COVID-TESTING-13209 | 4 Jul. 2022 | M | 47 | Transparent | Positive | 28 | Detected |
| KU-COVID-TESTING-13233 | 6 Jul. 2022 | F | 31 | Transparent | Positive | 30 | Detected |

TABLE 3 summarizes the results of Table 2:

| | | reference (PCR) | | |
|---|---|---|---|---|
| | | positive | negative | total |
| Biosensor | positive | 12 | 0 | 12 |
| | negative | 0 | 7 | 7 |
| | total | 12 | 7 | 19 |

The summary provided by Table 3 shows that the biosensor 100 was 100% sensitive and 100% selective in detecting SARS-CoV-2 in clinical samples.

Figures 28A, 28B, 28C, 28D:
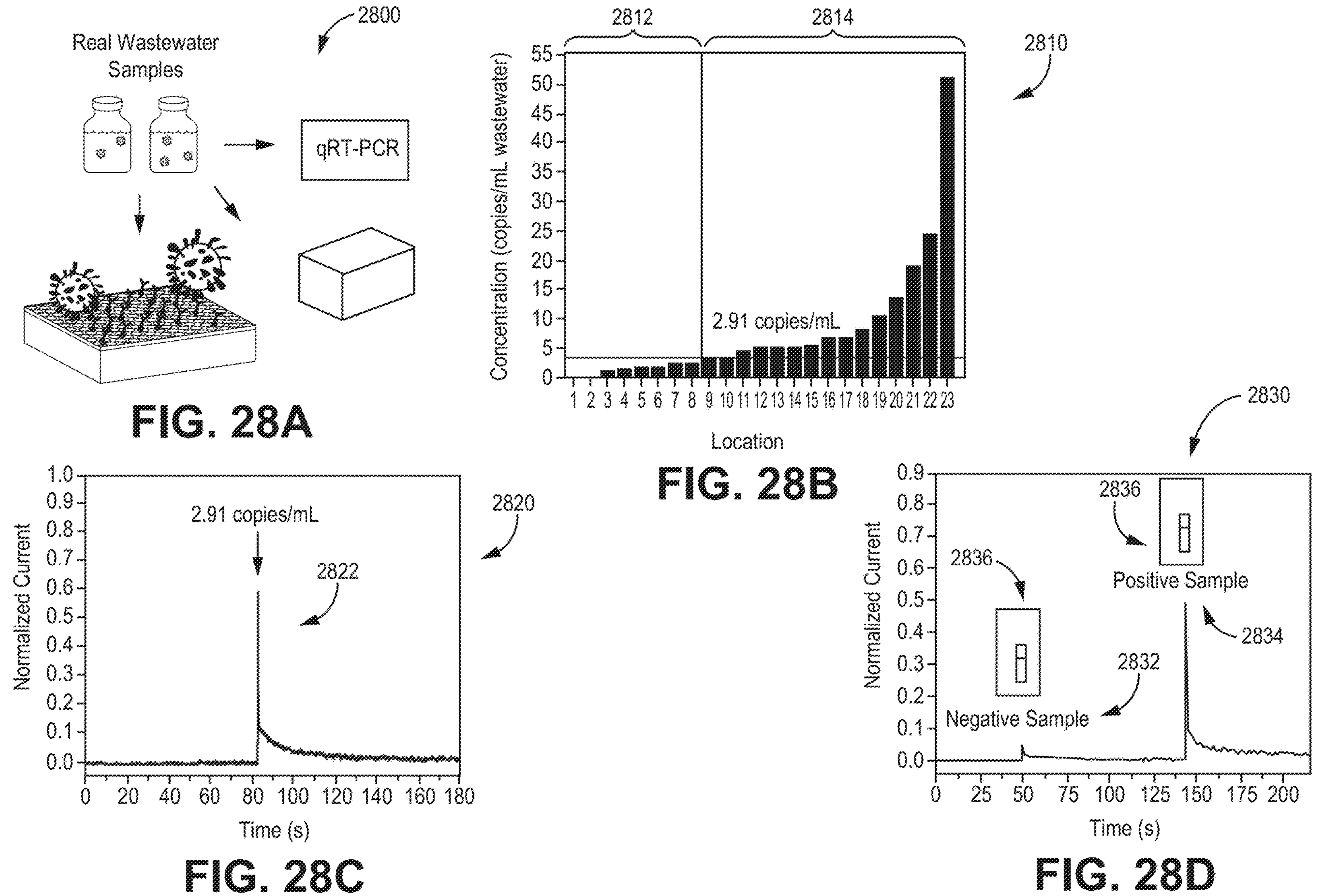
FIGS. 28A-D illustrates the performance of the rGO biosensor on municipal wastewater samples, according to some embodiments of this disclosure.

FIG. 28A illustrates a schematic diagram 2800 of municipal wastewater sample analysis by qRT-PCR, rapid antigen test, and the rGO biosensor 100. Autosamplers were used to collect 24 hour composite wastewater samples from a plurality of different locations. The results of qRT-PCR was used as the standard for comparison of the results obtained by the rapid antigen test and the rGO biosensor 100.

FIG. 28B illustrates a bar graph 2810 of the concentration of SARS-CoV-2 in the wastewater samples as determined by qRT-PCR. Samples 2814 with concentrations higher than 2.91 copies/mL tested positive using the rGO biosensor 100, while samples 2812 with concentrations less than 2.91 copies/mL did not test positive. The rGO biosensor 100 correctly identified 14/15 of the samples containing more than 2.91 copies/mL, depicting 93.3% accuracy above this threshold.

FIG. 28C illustrates a graph 2820 of the real-time response of the rGO biosensor 100 to a wastewater sample. qRT-PCR was utilized to determine that the wastewater sample had a viral concentration of 2.91 copies/mL. Curve 2822 illustrates that the response time of the rGO biosensor 100 to detect the virus was about 240 ms.

FIG. 28D illustrates a graph 2830 of the real-time response to samples from a negative location 2832 and a positive location 2834. Curve 2838 illustrates the performance of the rGO biosensor 100 and the photo inserts illustrate the performance of the rapid antigen based lateral flow test 2836. The rapid antigen tests 2836 failed to detect the virus in all the samples tested, including a sample with the highest concentration (50.78 copies/ml).

The rGO biosensor 100 detected SARS-CoV-2 in non-deactivated, unfiltered wastewater at concentrations as low as 0.23 copies/mL as determined by qRT-PCR. Only one positive sample was not detected by the rGO biosensor 100, highlighting a potentially very low false negative reporting rate by the rGO biosensor 100.

In summary, when configured to detect the SARS-CoV-2 S1 protein the rGO biosensor 100 achieved a LOD of 0.5 fg/mL in PBS and exhibited specificity against BSA protein, commercial vegan protein, glucosidase enzyme, and SARS-CoV-2 nucleocapsid protein (see FIGS. 27B and 27D). The response time of the rGO biosensor 100 was measured to be around 240 ms. The rGO biosensor 100 outperformed the rapid antigen test in identifying wastewater samples that were confirmed to contain the SARS-CoV-2 virus through qRT-PCR (see FIG. 28D). The rGO biosensor 100 identified positive wastewater samples with as little as 2.91 copies/mL as determined by qRT-PCR (see FIG. 28C).

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A method comprising:

applying an analyte to a rGO biosensor configured to bind to the analyte;

applying a DC voltage to the rGO biosensor while monitoring an electrical signal from the rGO biosensor, wherein the DC voltage is:

+0.0008V to +0.005V for a negatively charged analyte; or

−0.005V to −0.0008V for a positively charged analyte; and detecting a response to the analyte based on a change in the monitored electrical signal.

2. The method of claim 1, wherein the electrical signal is current, and monitoring the electrical signal comprises calculating a normalized current from the current and identifying a peak in the normalized current corresponding to the response to the analyte.

3. The method of claim 1, wherein the rGO biosensor comprises a reduced graphene oxide layer having a thickness of 20 nm to 60 nm and disposed on a substrate.

4. The method of claim 1, wherein the rGO biosensor comprises a reduced graphene oxide substrate and bioreceptors immobilized on the reduced graphene oxide substrate.

5. The method of claim 4, wherein the reduced graphene oxide substrate comprises:

a base; and five or more layers of reduced graphene oxide on the base.

6. The method of claim 5, wherein the five or more layers were formed by a graphene oxide solution with a concentration of 2 mg/mL and reduction of the graphene oxide to form the reduced graphene oxide substrate.

7. The method of claim 4, wherein the bioreceptors are antibodies immobilized to the rGO substrate by linker molecules.

8. The method of claim 7, wherein the linker molecules are PBASE molecules.

9. The method of claim 8, wherein PBASE molecules not coupled to an antibody are capped to prevent non-specific binding.

10. The method of claim 4, wherein the bioreceptors have a binding affinity to SARS-CoV-2.

11. The method of claim 2, wherein the normalized current is calculated relative to an initial baseline current measured prior to application of the analyte.

12. The method of claim 2, wherein identifying the peak in the normalized current comprises identifying the peak during real-time monitoring of the current after application of the analyte.

13. The method of claim 2, wherein the peak in the normalized current comprises a maximum in the normalized current relative to a baseline current.

14. The method of claim 2, wherein the peak is transient.

15. The method of claim 4, wherein the reduced graphene oxide substrate comprises seven layers of reduced graphene oxide.

16. The method of claim 1, wherein applying the analyte comprises at least one of:

immersing the rGO biosensor in a detection bath containing the analyte;

positioning the rGO biosensor within a conduit through which a fluid containing the analyte flows; or applying a liquid sample containing the analyte directly onto a surface of the rGO biosensor.

17. The method of claim 1, wherein applying the DC voltage comprises applying the DC voltage across electrical contacts coupled to the rGO biosensor.

18. A method of detecting an analyte using a reduced graphene oxide (rGO) biosensor, comprising:

applying the analyte to the rGO biosensor functionalized with a bioreceptor configured to bind the analyte;

applying a DC voltage across the rGO biosensor, wherein the DC voltage is:

+0.0008V to +0.005V for a negatively charged analyte; or

−0.005V to −0.0008V for a positively charged analyte;

measuring an electrical current through the rGO biosensor over time while the DC voltage is applied;

determining an initial baseline current prior to binding of the analyte to the rGO biosensor;

calculating a normalized current signal based on the measured electrical current relative to the initial baseline current; and detecting the analyte by identifying a peak in the normalized current signal indicative of binding of the analyte to the rGO biosensor.

* * * * *